US005474766A

United States Patent [19]
Schwartz et al.

[11] Patent Number: 5,474,766
[45] Date of Patent: Dec. 12, 1995

[54] METHODS AND COMPOSITIONS FOR INHIBITION OF HEPATIC CLEARANCE OF TISSUE-TYPE PLASMINOGEN ACTIVATOR

[75] Inventors: Alan L. Schwartz, Clayton; Guojun Bu, Chesterfield, both of Mo.

[73] Assignee: Washington University, St. Louis, Mo.

[21] Appl. No.: 992,827

[22] Filed: Dec. 18, 1992

[51] Int. Cl.$^6$ .......................... A61K 38/16; A61K 38/49; C07K 14/47
[52] U.S. Cl. ..................... 424/94.64; 424/94.63; 530/350; 530/395; 524/2; 524/8; 524/12
[58] Field of Search ................... 424/94.63, 94.64; 530/350, 395; 514/2, 12, 8

[56] References Cited

U.S. PATENT DOCUMENTS

| | | | |
|---|---|---|---|
| 4,791,068 | 12/1988 | Lostkutoff | 436/518 |
| 4,952,512 | 8/1990 | Loskutoff | 435/320.1 |
| 4,975,279 | 12/1990 | Schumacher | 424/94.63 |
| 4,997,847 | 3/1991 | Ife | 514/445 |
| 5,004,802 | 4/1991 | Kluft | 530/380 |
| 5,017,370 | 5/1991 | Hunter | 424/83 |
| 5,037,646 | 8/1991 | Higgins | 424/94.64 |
| 5,041,376 | 8/1991 | Gething | 435/172.3 |
| 5,073,540 | 12/1991 | Olsson | 514/3 |
| 5,078,995 | 1/1992 | Hunter | 424/78.38 |
| 5,116,964 | 5/1992 | Capon | 536/23.5 |

FOREIGN PATENT DOCUMENTS

| | | |
|---|---|---|
| 1282694 | 9/1991 | Canada . |
| WO84/01960 | 5/1984 | WIPO . |

OTHER PUBLICATIONS

Kanalas, J. et al., J. Am. Soc. Nephrol., 2: 547, abstract 41P, 1991.
Williams, S. E. et al. *Molecular Biology of the Cell*, 3: 298a, abstract 1732, 1992.
Makkar, S. P. et al., *American Pediatric Society*, Abstracts, p. 337A, abstract 2009, 1992.
Williams, S. et al.., *Biophys. J.*, 61 (2 Part 2):A95, Abstract 553, 1992.
Williams, S. E. et al. *J. Biol. Chem.*, 267(13):9035–40, 1992.
Makker, S. P. et al., *Clin. Res.* 40(2):336A, 1992.
Kounnas, M. Z. et al., *J. Biol. Chem.* 267(29):21162–66, 1992.
Kounnas, M. Z. et al., *J. Cell Biol.*, 115 (3 Part 2):251A, Abstract 1454, 1991.
Bu, G. et al., (1992) J. Biol. Chem. 267, 15595–15602.
Bu, G. et al., (1992) Proc. Natl. Acad. Sci. USA 89, 7427–7431.
Morton, P. A. et al., (1989) J. Biol. Chem. 264, 7228–7235.
Morton, P. A. et al., (1990) J. Biol. Chem. 265, 14093–14099.
Owensby, D. A. et al., (1988) J. Biol. Chem. 263, 10587–10594.
Owensby, D. A. et al., (1989) J. Biol. Chem. 264, 18180–18187.
Owensby, D. A. et al., (1991) J. Biol. Chem. 266, 4334–4340.
Schwartz, A. L. et al., (1981) J. Biol. Chem. 256, 8878–8881.
Schwartz, A. L. et al., (1983) J. Biol. Chem. 258, 11249–11255.
Schwartz, A. L. et al., (1982) J. Biol. Chem. 257, 4230–4237.
Schwartz, A. L. et al., (1984) CRC Crit. Rev. Biochem. 16, 207–233.
Underhill, D. M. et al., (1992) Blood 80, 2746–2754.
Ashcom, J. D. et al., (1990) J. Cell Biol. 110, 141–1048.
Bakhit, C. et al., (1988) Fibrin 2, 31–36.
Bakhit, C. et al., (1987) J. Biol. Chem. 262, 8716–8720.
Beebe, D. P. et al., (1986) Thromb. Res. 43, 663–674.
Beisiegel, U. et al., (1989) Nature 341, 162–164.
Bergmann, S. R. et al., (1983) Science, 220, 1181–1183.
Bounameaux, H. et al., (1986) Blood 67, 1493–1497.
Brown, M. S. et al., (1991) Cur. Opin. Lipidol. 2, 65–72.
Bugelski, P. J. et al., (1989) Thromb. Res. 53, 287–303.
Ciechanover et al., (1983) J. Biol. Chem. 258, 9681–9689.
Collen, D. et al., (1984) Circ. 70, 1012–1017.
Devries, S. R. et al., (1987) Fibrin. 1, 17–21.
Einarsson, M. et al., (1985) Thromb. Haemost. 54, 270, Abstract P1601.
Emies, J. J. et al., (1985) Thromb. Haemost. 54, 661–664.
Verstreate, M. et al. (1985) Lancet 1, 842–847.
Flameng, W. et al., (1985) J. Clin. Invest. 75, 84–90.
Fuchs, H. E. et al., (1985) Blood 65, 539–544.
Garabedian, H. D. et al., (1986) Am. J. Cardiol. 58, 673–679.
Herz, J. et al., (1988) EMBO J. 7, 4119–4127.
Herz, J. et al., (1991) J. Biol. Chem. 266, 21232–21238.
Higgins, D. L. et al., (1987) Biochem. 26, 7786–7791.
Jensen, P. H. et al., (1989) FEBS Lett. 255, 275–280.
Jorgensen, M. et al., (1987) Thromb. Haemostasis 58, 872–878.
Korninger, C. et al., (1981) Thromb. Haemostasis 46, 658–661.
Krause, J. et al., (1990) Biochem. J. 267, 647–652.
Krause, J. (1988) Fibrin. 2, 133–142.
Kuiper, J. et al., Fibrin, 2, 28 (1988), Abstract 57.
Kuiper, J. et al., (1988) J. Biol. Chem. 263, 18220–18224.
Laemmli, U. K., (1970) Nature 227, 680–685.
Levin, E. G., (1983) Proc. Natl. Acad. Sci. USA 80, 6804–6808.

(List continued on next page.)

*Primary Examiner*—Marianne P. Allen
*Attorney, Agent, or Firm*—Bryan Cave

[57] ABSTRACT

Methods and compositions for inhibiting the hepatic clearance of tissue-type plasminogen activator (t-PA) in vivo by administering a t-PA-hepatic clearance-inhibiting amount of 39 kDa protein or a t-PA-hepatic clearance-inhibiting fragment thereof, or genetically or chemically modified forms of the 39 kDa protein or fragments thereof are described. Methods and compositions for treatment of thrombolytic diseases by administering t-PA and a t-PA-hepatic clearance-inhibiting effective amount of 39 kDa protein, a t-PA-hepatic clearance inhibiting fragment thereof, and genetically or chemically modified forms of the 39 kDa protein or its fragments are described.

9 Claims, 21 Drawing Sheets

OTHER PUBLICATIONS

Lund, H. et al., (1989) Proc. Natl. Acad. Sci. USA 86, 9318–9322.

Matsudaira, P. T., *A Practical Guide to Protein and Peptide Purification for Microsequences,* pp. 52–57, (1989 Academic Press, NY).

Meyts, P. D. et al., (1976) J. Biol. Chem. 251, 1877–1888.

Nguyen, G. et al., (1992) J. Biol. Chem. 267, 6249–6256.

Nilsson, T. et al., (1984) Scand. J. Haematol. 33, 49–53.

Nilsson, S. et al., (1985) Thromb. Res. 39, 511–521.

Orth, K. et al., (1992) Proc. Natl. Acad. Sci. USA 89, 422–7426.

Petersen, L. C. et al., (1988) Biochim. Biophys. Acta 952, 245–254.

Ranby, M., (1982) Biochim Biophys. Acta 704, 461–469.

Rijken, D. C. et al., (1982) J. Biol. Chem. 257, 2920–2925.

Rijken, D. C. et al., (1990) Thromb. Res. Suppl. X. 63–71.

Rijken, D. C. et al., (1981) J. Biol. Chem. 256, 7035–7041.

Rijken, D. C. et al., (1986) Biochem. J. 238, 643–646.

Sprengers, E. D. et al., (1987) Blood 69, 381–387.

Sprengers, E. D. et al., (1985) J. Lab Clin. Med. 105, 751–758.

Strickland, D. K. et al., (1990) J. Biol. Chem. 265, 17401–17404.

Tate, K. M. et al., (1987) Biochem. 26, 338–343.

Thrombolysis in Myocardial Infarction Study Group, (1985) New Eng. J. Med. 312, 932–936.

Van de Werf, F. et al., (1984) New Eng. J. Med. 310, 609–613.

Van de Werf, F. et al., (1984) Circ. 69, 605–610.

Verstraete, M. et al., (1986) Thromb. Haemostas. 56, 1–15.

Wallen, P. et al., (1982) Biochim. Biophys. Acta 719, 318–328.

Yasuda, T. et al., (1988) J. Clin. Invest. 81, 1284–1291.

Einarsson, M. et al., (1988) Thromb. Haemost. 59, 474–479.

Furukawa, T. et al., (1990) 108, 297–302.

Moestrup, S. et al., (1989) J. Biol. Chem. 264, 15574–15577.

Nykjaer, A. et al., (1992) J. Biol. Chem. 267, 14543–14546.

Otter, M. et al., (1992) Biochem. J. 284, 545–550.

Pietromonaco, S. et al., (1990) Proc. Natl. Acad. Sci. U.S.A. 87, 1811–1815.

Strickland, D. et al., (1991) J. Biol. Chem. 266, 13364–13369.

Williams, S. et al., (1992) J. Biol. Chem. 267, 9035–9040.

Moestrup, S. K. et al., *J. Biol. Chem.,* 266(21):14011–14017, 1991.

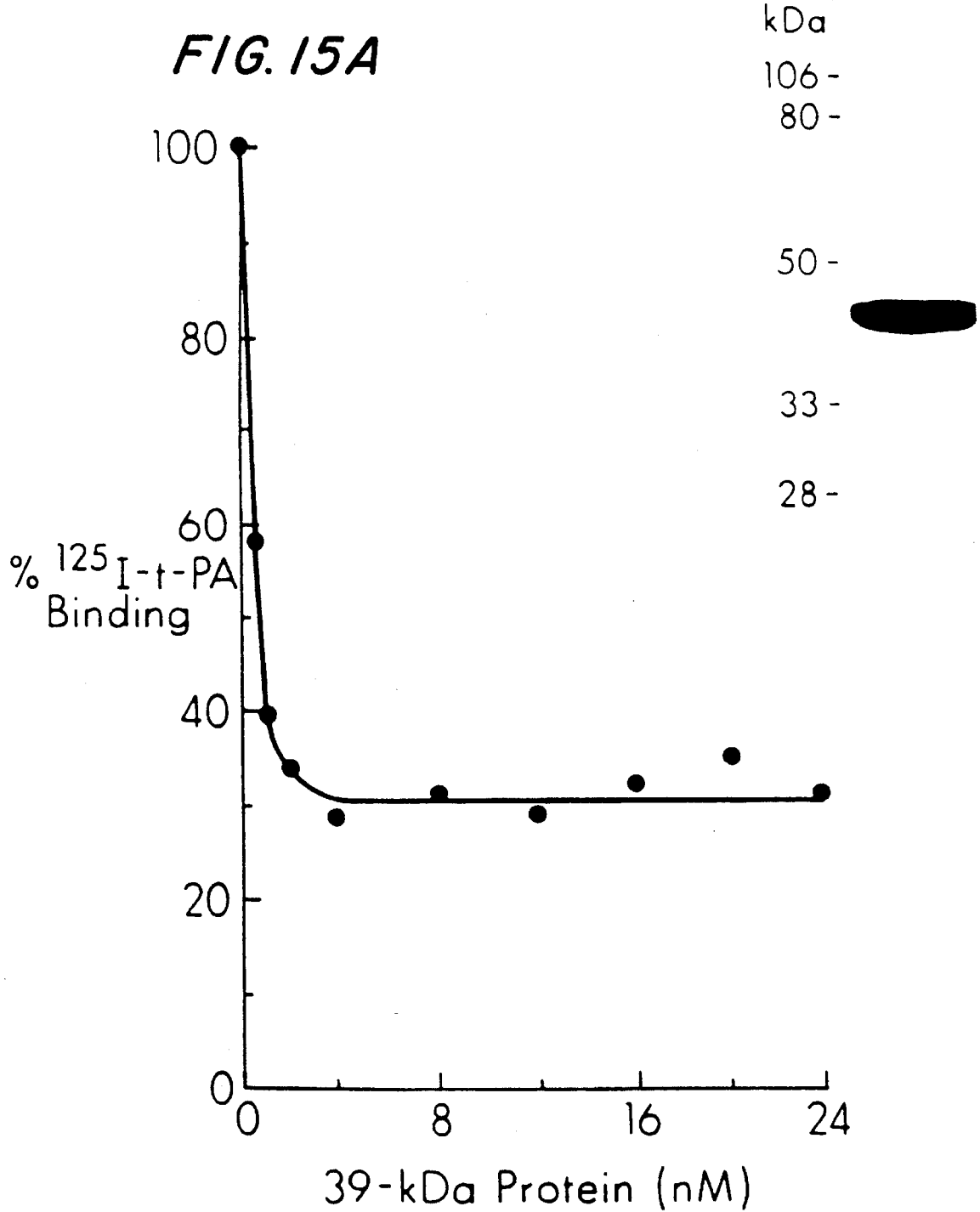

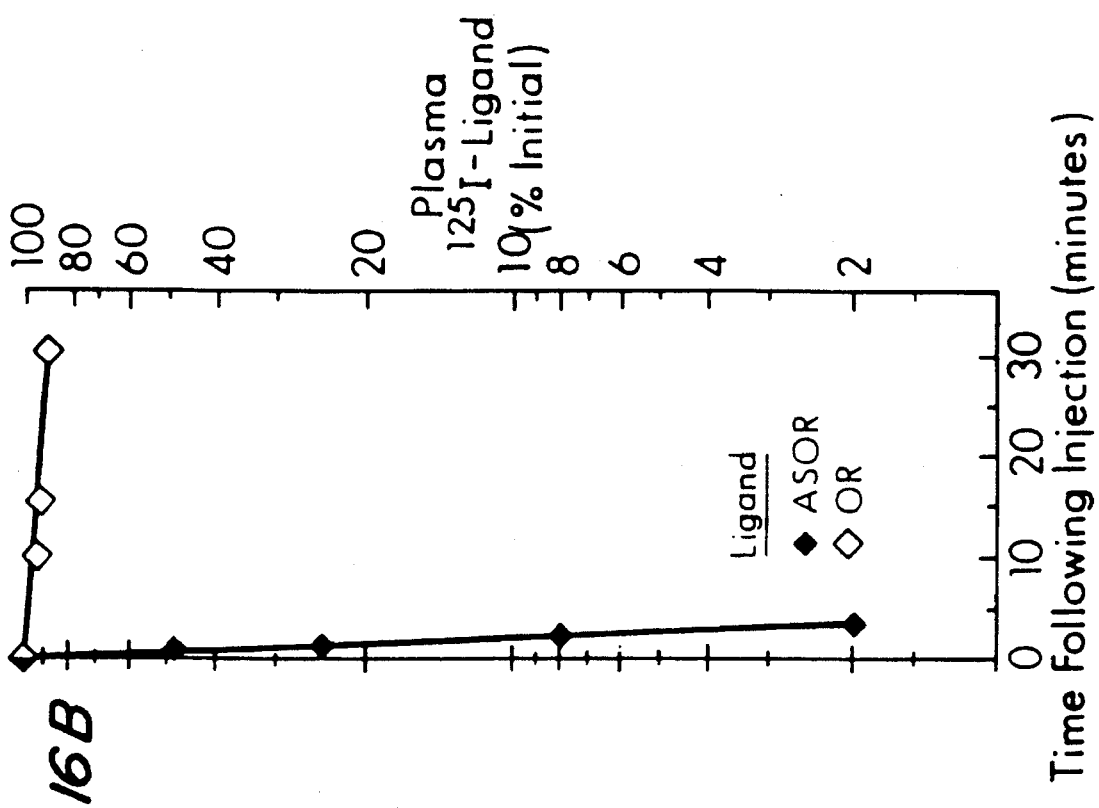
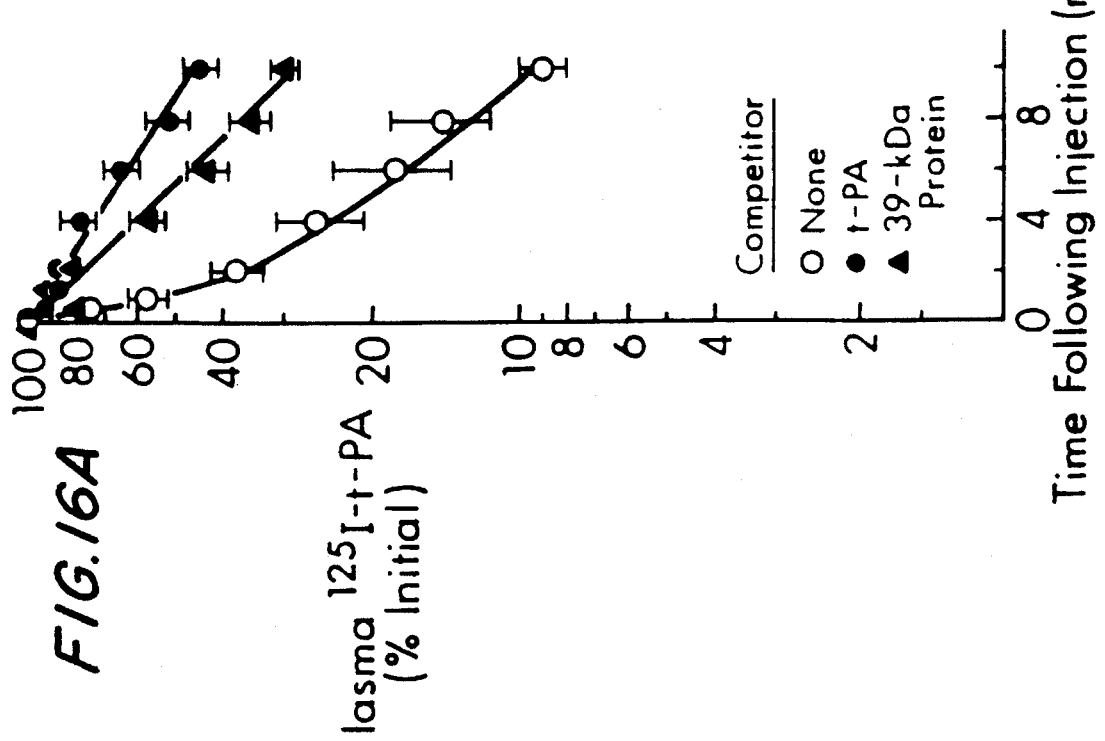
FIG.16B
FIG.16A

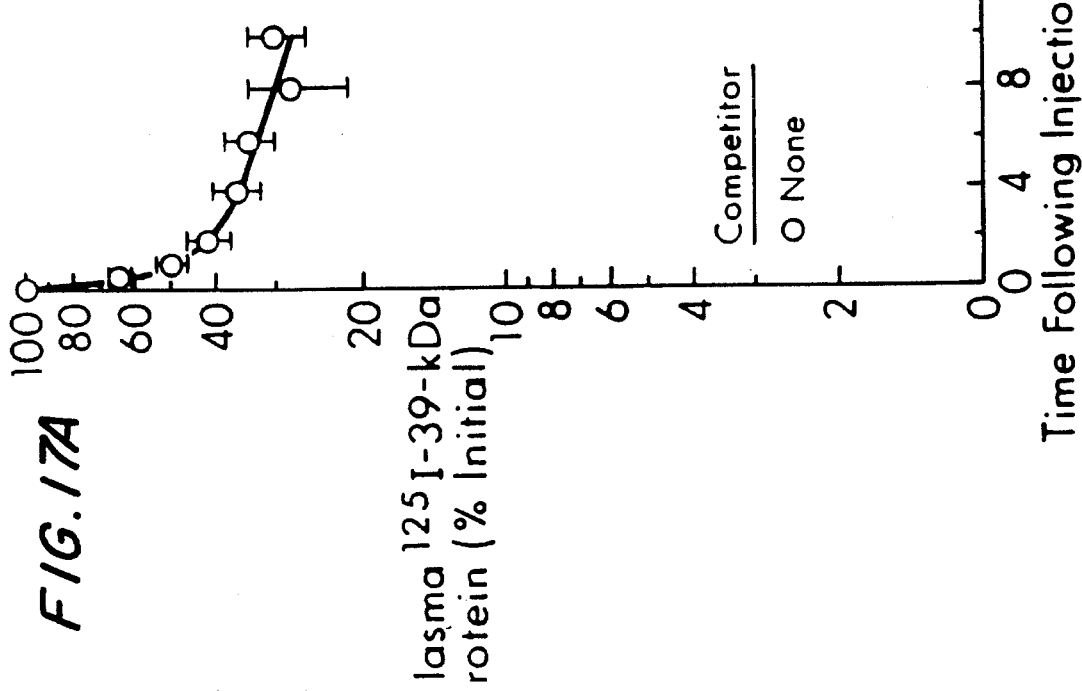

METHODS AND COMPOSITIONS FOR INHIBITION OF HEPATIC CLEARANCE OF TISSUE-TYPE PLASMINOGEN ACTIVATOR

This invention was made with government support under HL 17646 awarded by the National Institutes of Health. The government has certain rights in the invention.

FIELD OF THE INVENTION

This invention relates to methods and compositions for inhibiting the hepatic clearance of tissue-type plasminogen activator (t-PA) in vivo comprising administering a t-PA-hepatic clearance-inhibiting amount of 39 kDa protein or a t-PA-hepatic clearance-inhibiting fragment thereof, or genetically or chemically modified forms of the 39 kDa protein or fragments thereof; and to methods and compositions for treatment of thrombolytic diseases comprising administering t-PA and a t-PA-hepatic clearance-inhibiting effective amount of 39 kDa protein, a t-PA-hepatic clearance inhibiting fragment thereof, and genetically or chemically modified forms of the 39 kDa protein or its fragments.

BACKGROUND OF THE INVENTION

Tissue plasminogen activator is an enzyme widely used as a thrombolytic agent in the treatment of acute myocardial infarction. t-PA is secreted from endothelial cells as a single polypeptide chain that is subsequently cleaved (between $Arg_{275}$ and $Ile_{276}$) into two chains held together by a single disulfide bond (Rijken, D. C. et al., (1981) J. Biol. Chem. 256, 7035–7041. Both the single- and two-chain forms of the enzyme can bind to fibrin (Rijken, D. C. et al., (1982) J. Biol. Chem. 257, 2920–2925; Higgins, D. L. et al., (1987) Biochem. 26, 7786–7791), although the two-chain form is catalytically more active (Wallen, P. et al., (1982) Biochim. Biophys. Acta 719, 318–328; Ranby, M., (1982) Biochim Biophys. Acta 704, 461–469; Tate, K. M. et al., (1987) Biochem. 26, 338–343; and Petersen, L. C. et al., (1988) Biochim. Biophys. Acta 952, 245–254). In addition, both forms of the enzyme (Jorgensen, M. et al., (1987) Thromb. Haemostasis 58, 872–878) are inactivated by a fast-acting plasminogen activator inhibitor (type 1)(PAI-1), a member of the serpin family that is secreted from endothelial cells and forms a covalent bond with $Ser_{478}$ of t-PA (Levin, E. G., (1983) Proc. Natl. Acad. Sci. USA 80, 6804–6808; and Sprengers, E. D. et al., (1987) Blood 69, 381–387).

Exogenously administered t-PA is capable of eliciting prompt thrombolysis in therapeutic doses that do not produce marked fibrinolysis in experimental animals with induced coronary artery thrombosis (Bergmann, S. R. et al., (1983) Science, 220, 118114 1183) and in patients with evolving myocardial infarction (Van de Werf, F. et al., (1984) New Eng. J. Med. 310, 609–613; Collen, D. et al., (1984) Circ. 70, 1012–1017; Van de Werf, F. et al., (1984) Circ. 69, 605–610; Thrombolysis in Myocardial Infarction Study Group, (1985) New Eng. J. Med. 312, 932–936; and European Cooperative Study Group, (1985) Lancet 1, 842–847). However, because the clearance of t-PA from the circulation is so rapid, continuous infusions have been required.

In vivo studies of t oPA clearance have been performed in a variety of species including mice (Fuchs, H. E. et al., (1985) Blood 65, 539–544); rats (Emeis, J. J. et al., (1985) Thromb. Haemost. 54, 661–664; Rijken, D. C. et al., (1986) Biochem. J. 238, 643–646; Kuiper, J. et al., (1988) J. Biol. Chem. 263, 18220–18224; Bakhit, C. et al., (1988) Fibrin. 2, 31–36; Krause, J. et al., (1990) Biochem. J. 267, 647–652); rabbits (Korninger, C. et al., (1981) Thromb. Haemostasis 46, 658–661; Bounameaux, H. et al., (1986) Blood 67, 1493–1497); dogs (Devries, S. R. et al., (1987) Fibrin. 1, 17–21; Yasuda, T. et al., (1988) J. Clin. Invest. 81, 1284–1291); and monkeys (Flameng, W. et al., (1985) J. Clin. Invest. 75, 84–90. These studies together with experiments in man (Garabedian, H. D. et al., (1986) Am. J. Cardiol. 58, 673–679; Verstraete, M. et al., (1986) Thromb. Haemostas. 56, 1–15) demonstrate the rapid removal of t-PA from the circulation, which varies from about $tu_{1/2}$=1 min in rats to $t_{1/2}$5 min in man.

The liver appears to be the major site of removal and catabolism of t-PA (Nilsson, T. et al., (1984) Scand. J. Haematol. 33, 49–53; Devries, S. R. et al., (1987) Fibrin. 1, 17–21; Korninger, C. et al., (1981) Thromb. Haemostasis 46, 658–661; Bounameaux, H. et al., (1986) Blood 67, 1493–1497; Beebe, D. P. et al., (1986) Thromb. Res. 43, 663–674; Nilsson, S. et al., (1985) Thromb. Res. 39, 511–521; Emeis, J. J. et al., (1985) Thromb. Haemost. 54, 661–664; Rijken, D. C. et al., (1986) Biochem. J. 238, 643–646; Fuchs, H. E. et al., (1985) Blood 65, 539–544; and Kuiper, J. et al., (1988) J. Biol. Chem. 263, 18220–18224). About 80% of exogenous t-PA delivered intravascularly rapidly accumulates in the liver and is subsequently degraded, with subsequent appearance of degradation products in plasma. These studies support a general clearance mechanism for t-PA in which uptake and degradation within the liver is followed by the release of the degradation products initially into the blood and subsequently into the urine.

Further, the half-life of circulating t-PA is markedly prolonged in animals subjected to hepatectomy (Bounameaux, H. et al., (1986) Blood 67, 1493–1497; and Nilsson, T. et al., (1984) Scand. J. Haematol. 33, 49–53). Neither the protease active site nor a specific glycosylation pattern appears to be a major determinant of hepatic recognition and degradation of t-PA in vivo (Fuchs, H. E. et al., (1985) Blood 65, 539–544), in perfused liver systems (Emeis, J. J. et al., (1985) Thromb. Haemost. 54, 661–664, or in isolated hepatocytes (Bakhit, C. et al., (1987) J. Biol. Chem. 262, 8716–8720. The clearance and catabolism of t-PA has been reviewed in detail (Krause, J. (1988) Fibrin. 2, 133–142). However, information is limited regarding the particular cell type responsible for clearance of t-PA.

After administration of fluorescent or radiolabelled t-PA to rats and subfractionation of the livers into parenchymal, endothelial, and Kupffer cells, it was found that parenchymal and endothelial cells constitute the major sites for hepatic uptake (Fuchs, H. E. et al., (1985) Blood 65, 539–544; Sprengers, E. D. et al., (1987) Blood 69, 381–387; Kuiper, J. et al., Fibrin, 2:28 (1988) and Bugelski, P. J. et al., (1989) Thromb. Res. 53, 287–303).

The uptake of t-PA into all liver cell types is inhibited by in vivo competition with unlabelled t-PA whereas glycoproteins such as mannan and ovalbumin inhibit the specific uptake of labelled t-PA in isolated liver endothelial cells. The endocytosis of t-PA is mediated, at least in part, by mannose receptors on endothelial cells (Einarsson, M. et al., (1985) Thromb. Haemost. 54, 270; and Kuiper, J. et al., (1988) Fibrin. 2, 28). Monensin, $NH_4Cl$, and cytochalasin B block the uptake and degradation of t-PA, indicating that the uptake is endocytotic and that the degradation is lysosomal. In hepatoma cell lines, representing parenchymal cells, t-PA clearance involves ligand binding, uptake, and degradation mediated by a high capacity, high-affinity specific receptor system (Owensby, D. A. et al., (1988) J. Biol. Chem. 263, 10587–10594). Subfractionation of rat liver parenchymal, endothelial, and Kupffer cells 5 minutes after $^{125}$I-t-PA injection revealed that liver parenchymal cells are responsible for about 55% of the cleared $^{125}$I-t-PA, endothelial cells for about 40%, and Kupffer cells for about 5% (Kuiper, J. et al., (1988) J. Biol. Chem. 263, 18220–18224; Rijken, D.C. et al., (1990) Thromb. Res. Suppl. X, 63–71).

Two distinct mechanisms for t-PA catabolism by hepatoma cells have been shown. t-PA complexed to PAI-1 is recognized by a PAI-1 dependent receptor on the cell surface of human hepatoma HepG2 cells (Schwartz, A. L. et al., (1981) J. Biol. Chem. 256, 8878–8881; Owensby, D. A. et al., (1988) J. Biol. Chem. 263, 10587–10594; Morton, P. A. et al., (1989) J. Biol. Chem. 264, 7228–7235; Bu, G. et al., (1992) J. Biol. Chem. 267, 15595–15602). t-PA in the absence of bioactive PAI-1 has been found to bind to PAI-1 independent receptors which mediate binding and endocytosis of t-PA on rat hepatoma $MH_1C_1$ cells (Bu, G. et al., (1992) J. Biol. Chem. 267, 15595-15602) and on rat Novikoff hepatoma cells (Nguyen, G. et al., (1992) J. Biol. Chem. 267, 6249–6256). Although this PAI-1 independent t-PA clearance system has not been reported on human hepatocytes, the rapid clearance of intravenously injected t-PA, normally at a level far exceeding the available PAI-1, suggests the existence of a PAI-1 independent t-PA clearance system.

At present, t-PA is administered clinically in the form of an initial bolus that is followed by sustained infusion. The total amount of enzyme administered during a standard 3 hour treatment is 50–100 mg. Such large amounts are required for two reasons: first, to counterbalance the effects of the rapid clearance of t-PA from the circulation, and second, to overcome the effects of high concentrations of fast-acting inhibitors of the enzyme that are present in plasma and platelets. When high doses are used in an effort to increase the rate of clot lysis or to lyse refractory clots, there is a risk of systemic fibrinolysis which affects the body's capacity to stop bleeding and hemorrhage.

Reducing the rate of t-PA clearance from the circulation following administration would provide a significant advantage in clinical use. This would allow t-PA to be administered in much smaller doses than are currently required, thereby reducing, e.g., the risk of systemic fibrinolysis and hemorrhage. Accordingly, an objective of the invention is to provide methods and compositions for the inhibition of hepatic clearance of t-PA. Another objective of the invention is to provide a method and composition for the treatment of thrombolytic diseases which allows t-PA to be administered in much smaller doses than currently required. These and other objectives and features of the invention will be apparent from the following description.

BRIEF DESCRIPTION OF THE DRAWINGS

FIG. 2A is a graph of the saturation binding of $^{125}$I-t-PA in the absence or presence of 1 μM unlabelled t-PA. (squares)=total ligand binding; (triangles)=non-specific ligand binding; (circles)= specific binding calculated as the difference between total and non-specific binding. Symbols represent the means of triplicate determinations. The inset is a Scatchard plot of specific binding, where B=bound $^{125}$I-t-PA, B/F=bound/free $^{125}$I-t-PA. FIG. 2B is a graph of the saturation binding of the $^{125}$I-39 kDa protein. The same symbols are used as in FIG. 2A. The inset, like FIG. 2A, is a Scatchard plot of specific binding.

In FIGS. 3A and 3B, $MH_1C_1$ cells were incubated in the presence of 0.5 mM DTSSP for 1 hour. In FIGS. 3C and 3D, $MH_1C_1$ cells were incubated in the absence of 0.5 mM DTSSP for 1 hour. Cells were then lysed and immunoprecipitated with normal rabbit serum (lanes 1 and 4), anti-LRP serum (lanes 2 and 5), or anti-39 kDa protein serum (lanes 3 and 6). In FIGS. 3A and 3C, the SDS-PAGE gels were analyzed under nonreducing conditions. In FIGS. 3B and 3D, the SDS-PAGE gels were analyzed under reducing conditions. Gels from samples incubated in the presence of cross-linker were autoradiographed for 3 days at −70° C.; gels incubated in the absence of cross-linker were autoradiographed for only 2 days. The position of $^{125}$I-39 kDa protein (closed arrowhead) is indicated.

FIG. 4A is a SDS-PAGE gel (7.5% acrylamide) analyzed under nonreducing conditions. FIG. 4B is a SDS-PAGE gel (7.5% acrylamide) analyzed under reducing conditions. The region of cross-linked material is marked with a bracket. The positions of $^{125}$I-t-PA (closed arrow) and $^{125}$I-t-PA:PAI-1 (open arrow) are indicated.

Figure 7A:
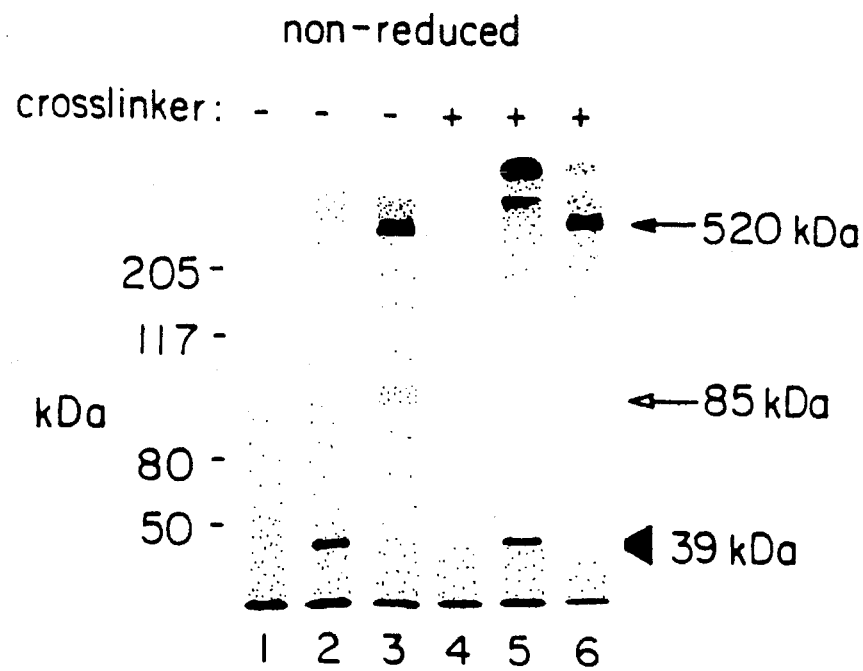
Figure 7B:
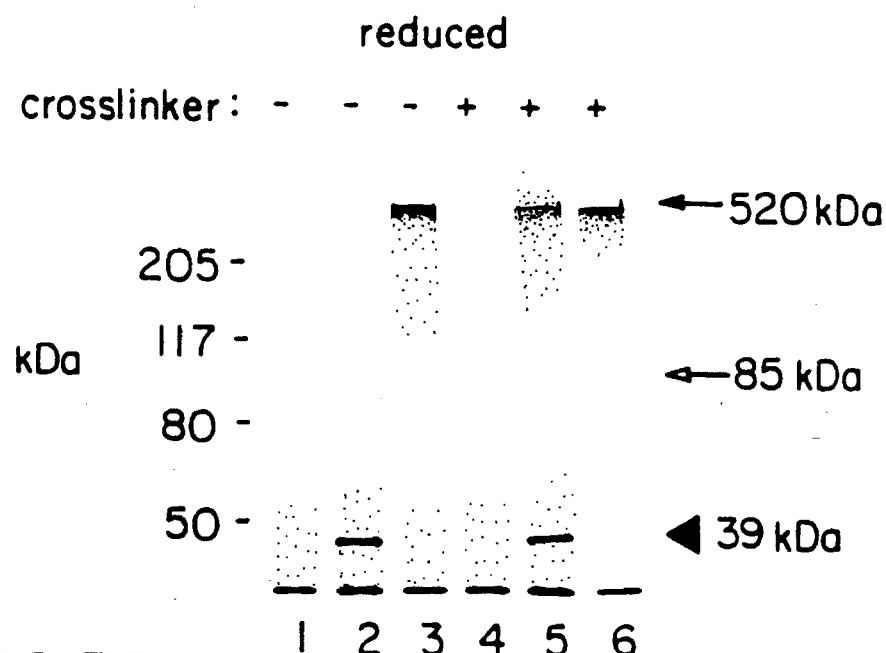

FIGS. 7A–B are SDS-PAGE gels (8.5% acrylamide) of cross-linking of unlabelled 39 kDa protein to the cell surface of metabolically labelled rat $MH_1C_1$ cells. Cell monolayers in lanes 4–6 were incubated for 1 hour with 0.5 mM DTSSP, whereas cell monolayers in lanes 1–3 were incubated for 1 hour in PBSc alone. Cells were then lysed and immunoprecipitated with either normal rabbit serum (lanes 1 and 4), affinity purified α-rat 39 kDa protein (lanes 2 and 5), or affinity purified α-human LRP (lanes 3 and 6). In FIG. 7A, the SDS-PAGE gel was analyzed under nonreducing conditions. In FIG. 7B, the SDS-PAGE gel was analyzed under reducing conditions. The closed arrowhead indicates the position of the 39 kDa protein. The open and closed arrows indicate, respectively, the positions of the 85 kDa and 520 kDa subunits of LRP.

Figure 8A:
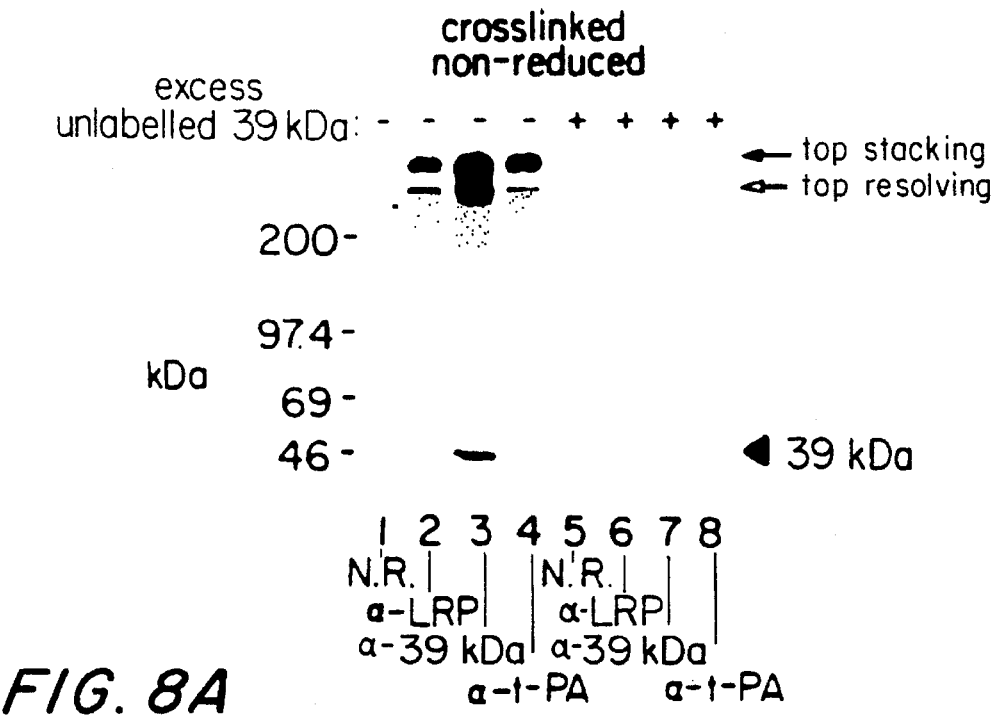
Figure 8B:
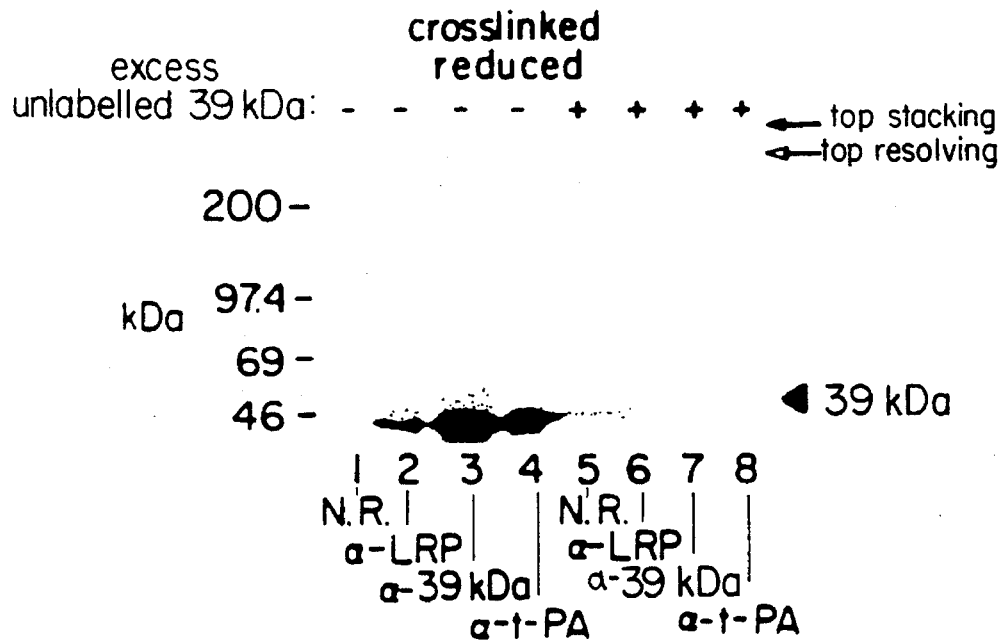
Figure 8C:
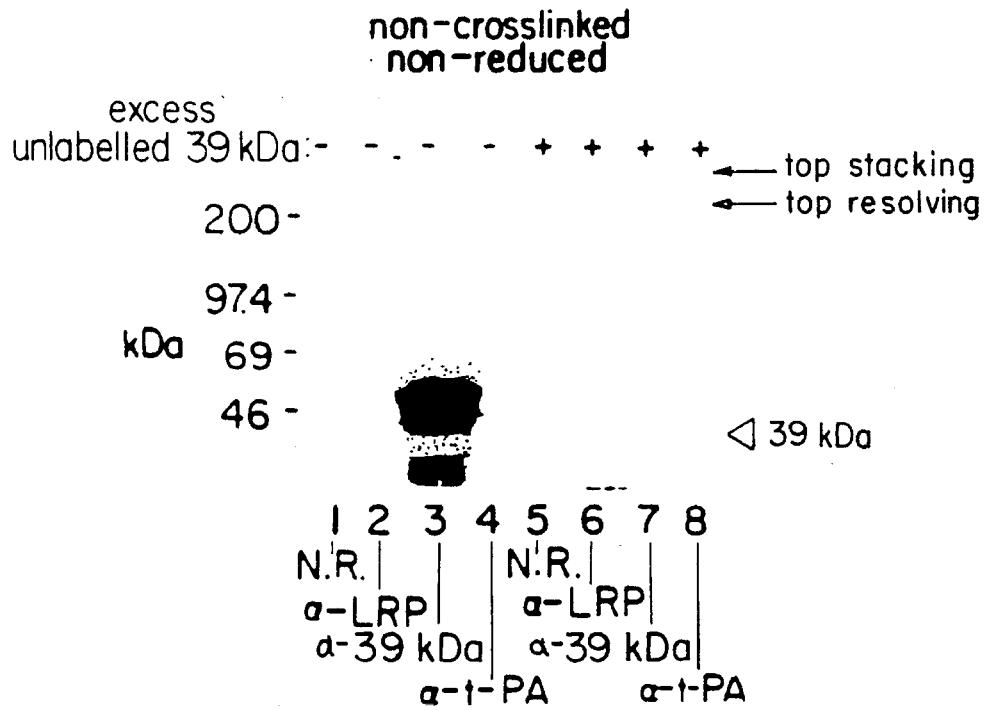
Figure 8D:
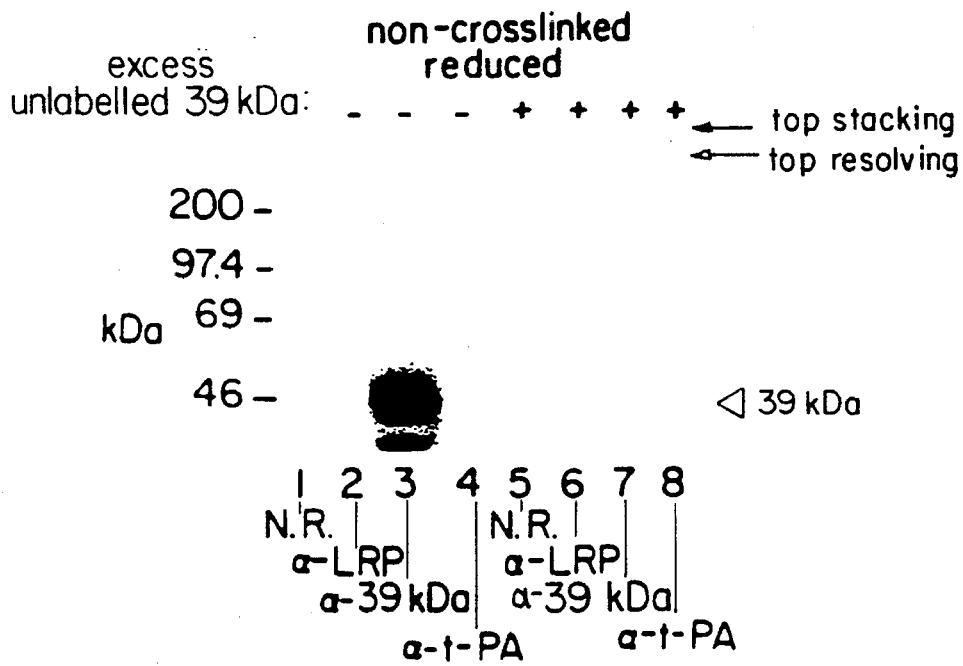
Figure 8E:
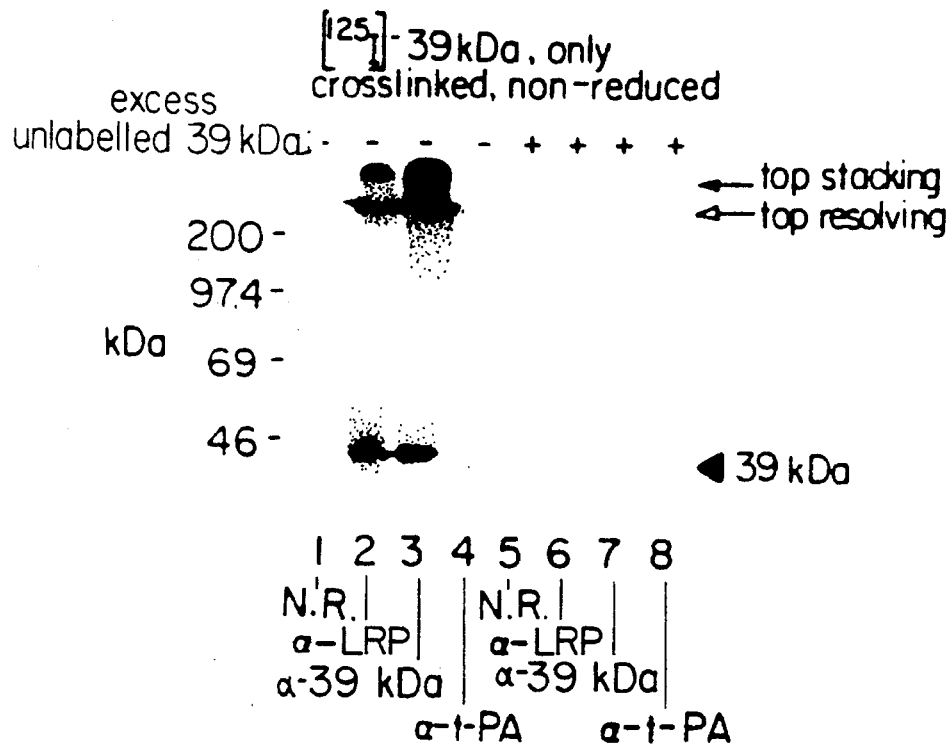
Figure 8F:
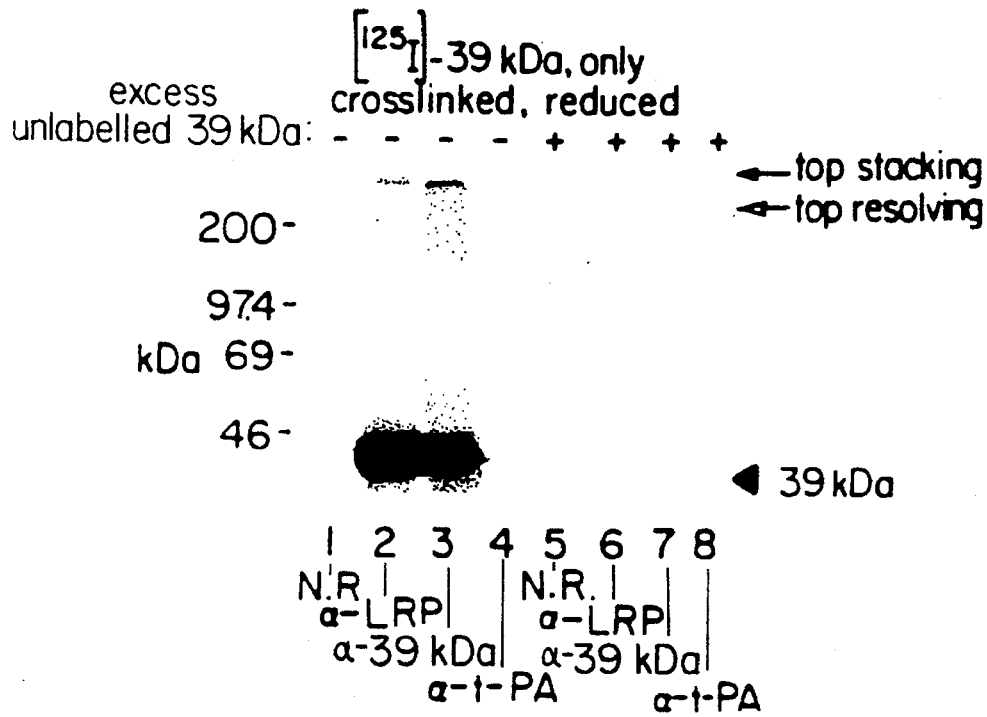

FIGS. 8A–F are SDS-PAGE gels (8.5% acrylamide) of co-binding and cross-linking of $^{125}I$-39 kDa protein and unlabelled t-PA to rat $MH_1C_1$ cells in the presence or absence of 0.5 μM unlabelled 39 kDa protein. In FIGS. 8A, 8C, and 8E, the SDS-PAGE gels were analyzed under nonreducing conditions. In FIGS. 8B, 8D, and 8F, the SDS-PAGE gels were analyzed under reducing conditions.

Figure 9:
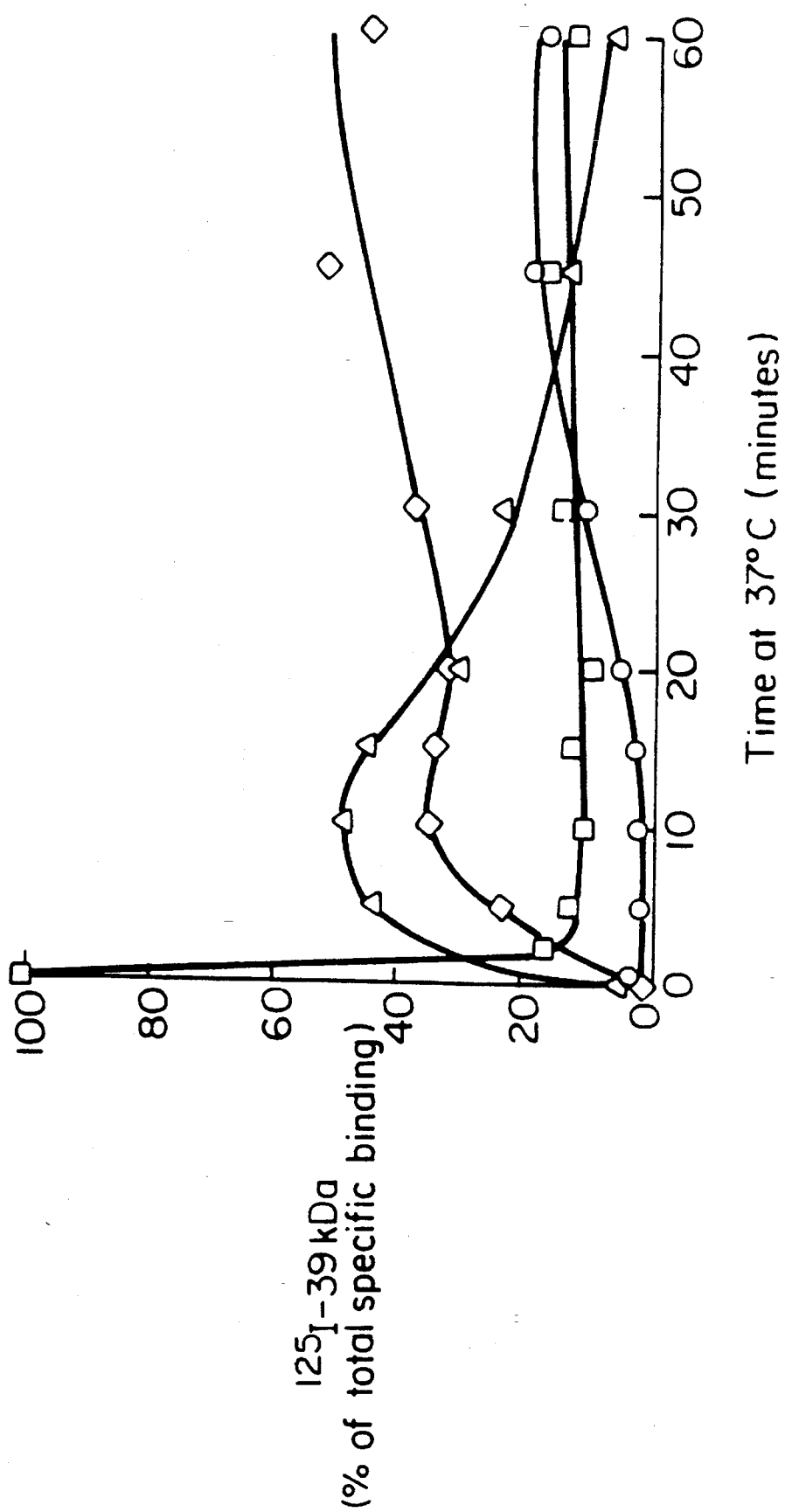

FIG. 9 is a graph of rapid endocytosis and degradation of surface bound $^{125}I$-39 kDa protein by $MH_1C_1$ cells in the presence and absence of 0.5 μM unlabelled 39 kDa protein. (circles, degraded ligand)=TCA soluble radioactivity; (diamonds, both dissociated and degraded ligand)=total radioactivity; (squares, plasma membrane associated)=Pronase sensitive ligand; (triangles, cell associated)=Pronase resistant ligand. Each data point represents specific radioactivity (i.e., the difference of total and non-specific radioactivity) and is the mean of triplicate determinations.

Figure 10A:
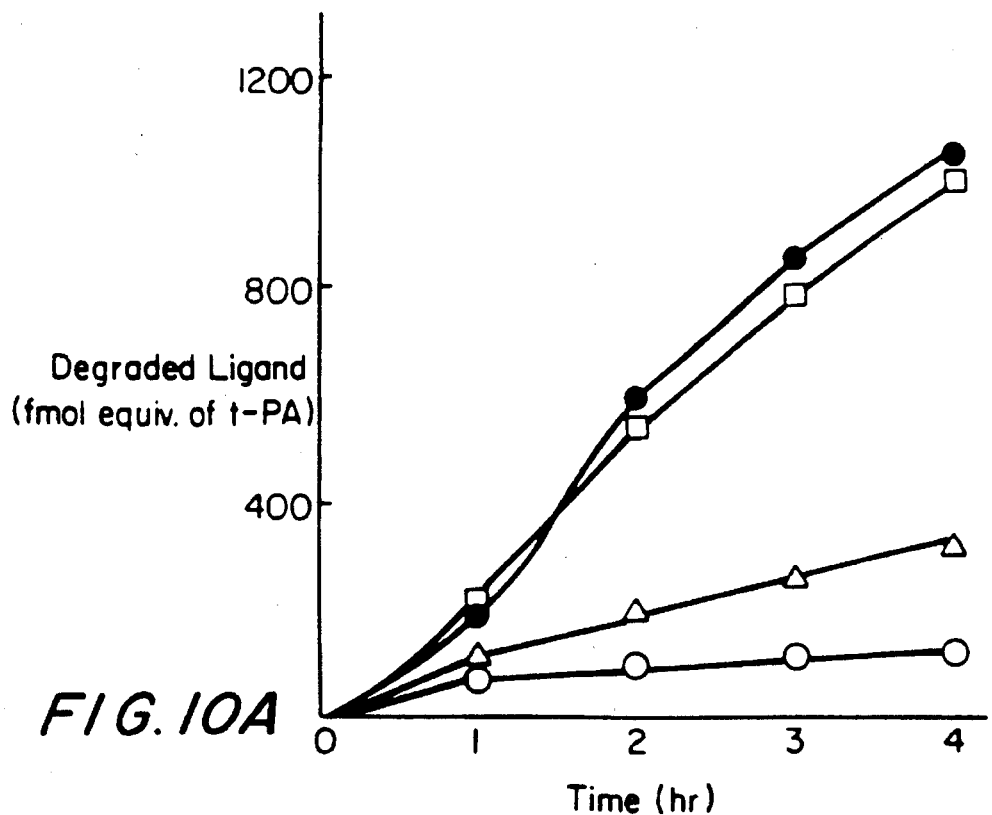
Figure 10B:
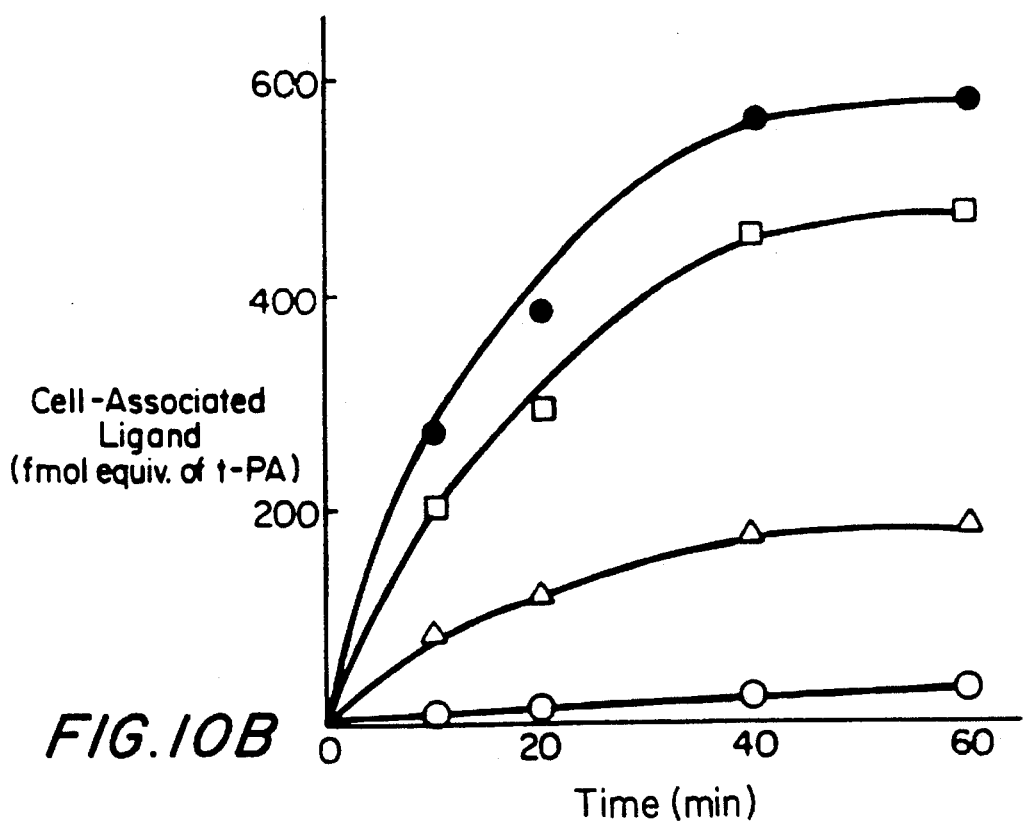

FIGS. 10A–B are graphs of the inhibition of $^{125}I$-t-PA uptake and degradation by the 39 kDa protein on HepG2 cells. (open squares)=prewarmed (37° C.) binding buffer containing $^{125}I$-t-PA (3 nM); (open circles)=prewarmed (37° C.) binding buffer containing $^{125}I$-t-PA (3 nM) in the presence of 1 μM concentration of t-PA; (open triangles)= prewarmed (37° C.) binding buffer containing $^{125}I$-t-PA (3 nM) in the presence of 1 μM concentration of the 39-kDa protein; (closed circles)=prewarmed (37° C.) binding buffer containing $^{125}I$-t-PA (3 nM) in the presence of 1 μM concentration of BSA. FIG. 10A shows TCA soluble radioactivity representing the degraded ligands in fmoles equivalents of t-PA. FIG. 10B shows the radioactivity associated with each cell lysate in fmoles equivalents of t-PA. In each graph, each symbol represents the average of triplicate determinations and the standard deviations were less than 5%.

Figure 11A:
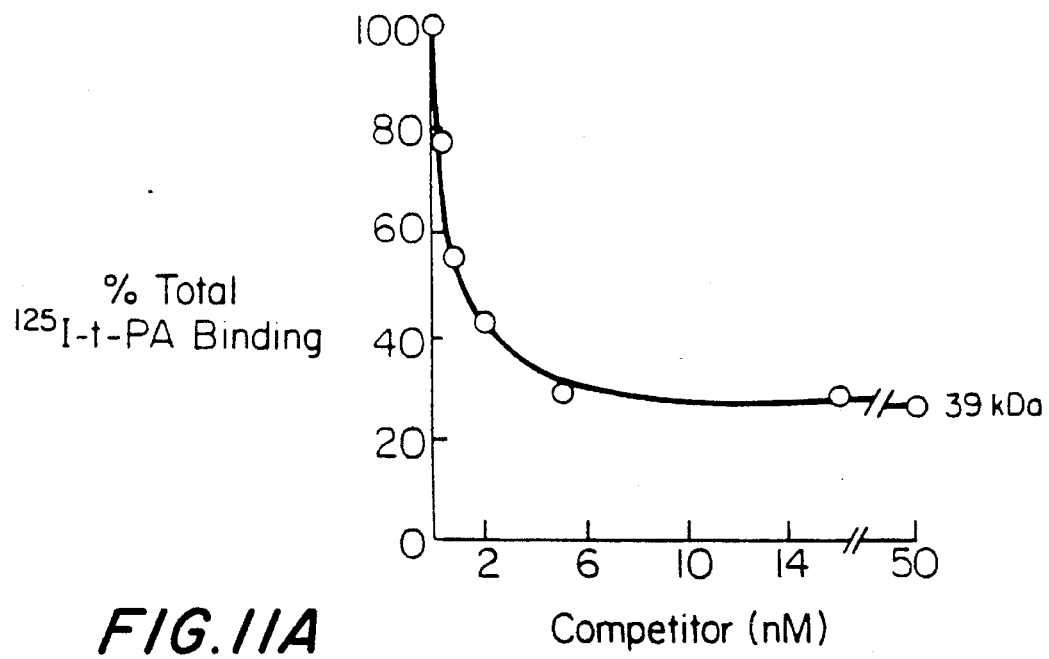
Figure 11B:
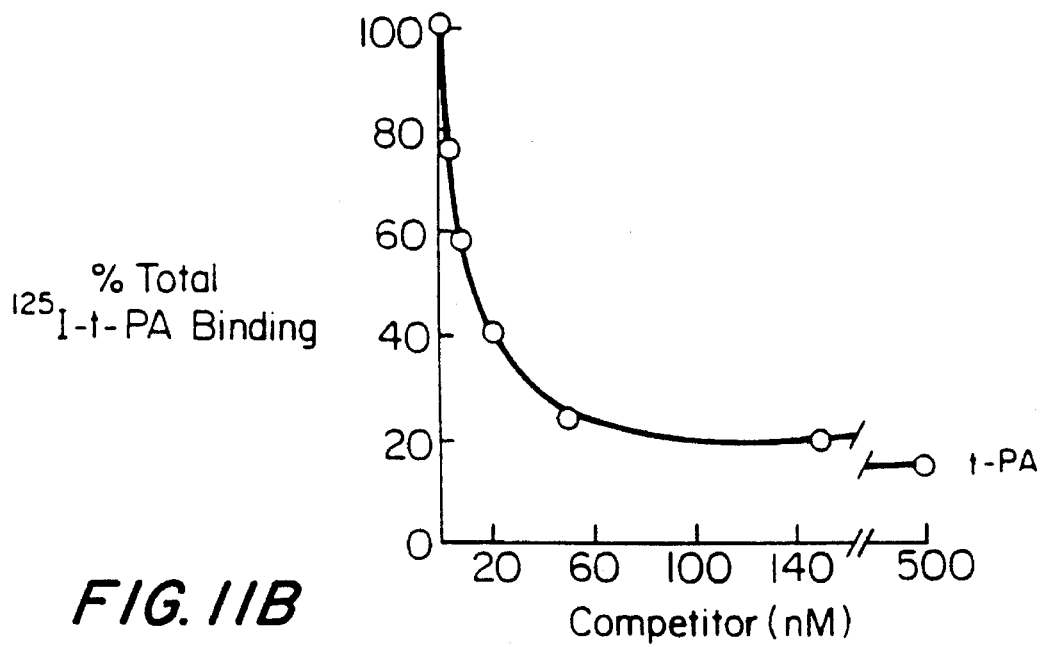

FIGS. 11A–B are graphs of the inhibition of $^{125}I$-t-PA binding by rat 39 kDa protein on $MH_1C_1$ cells in the presence of increasing concentrations of either unlabelled t-PA or 39 kDa protein. Each point represents the mean of triplicate determinations. FIG. 13A shows the inhibition of $^{125}I$-t-PA binding by the 39 kDa protein. FIG. 13B shows the inhibition of $^{125}I$-t-PA binding by unlabelled t-PA.

Figure 12:
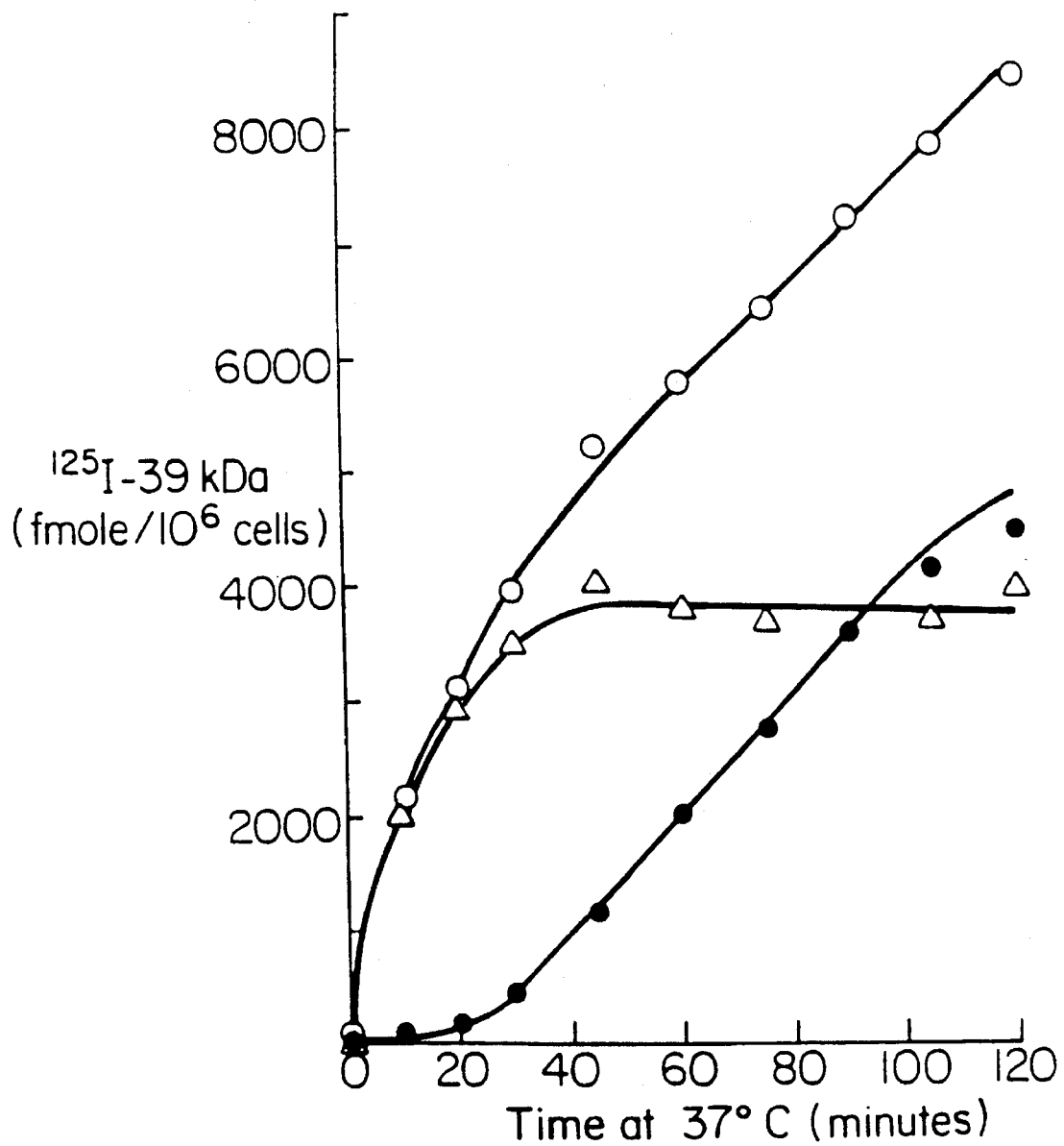

FIG. 12 is a graph of the rapid uptake and degradation of $^{125}I$-39 kDa protein by rat $MH_1C_1$ cells at 37° C. Closed circles represent TCA soluble counts (internalized and degraded ligand) in the extracellular media. Triangles indicate the amount of cell associated radioactivity as determined following lysis of the cell monolayers. Open circles represent the sum of both cell associated and extracellular degraded ligand. Each point is the mean of triplicate determinations.

Figure 13:
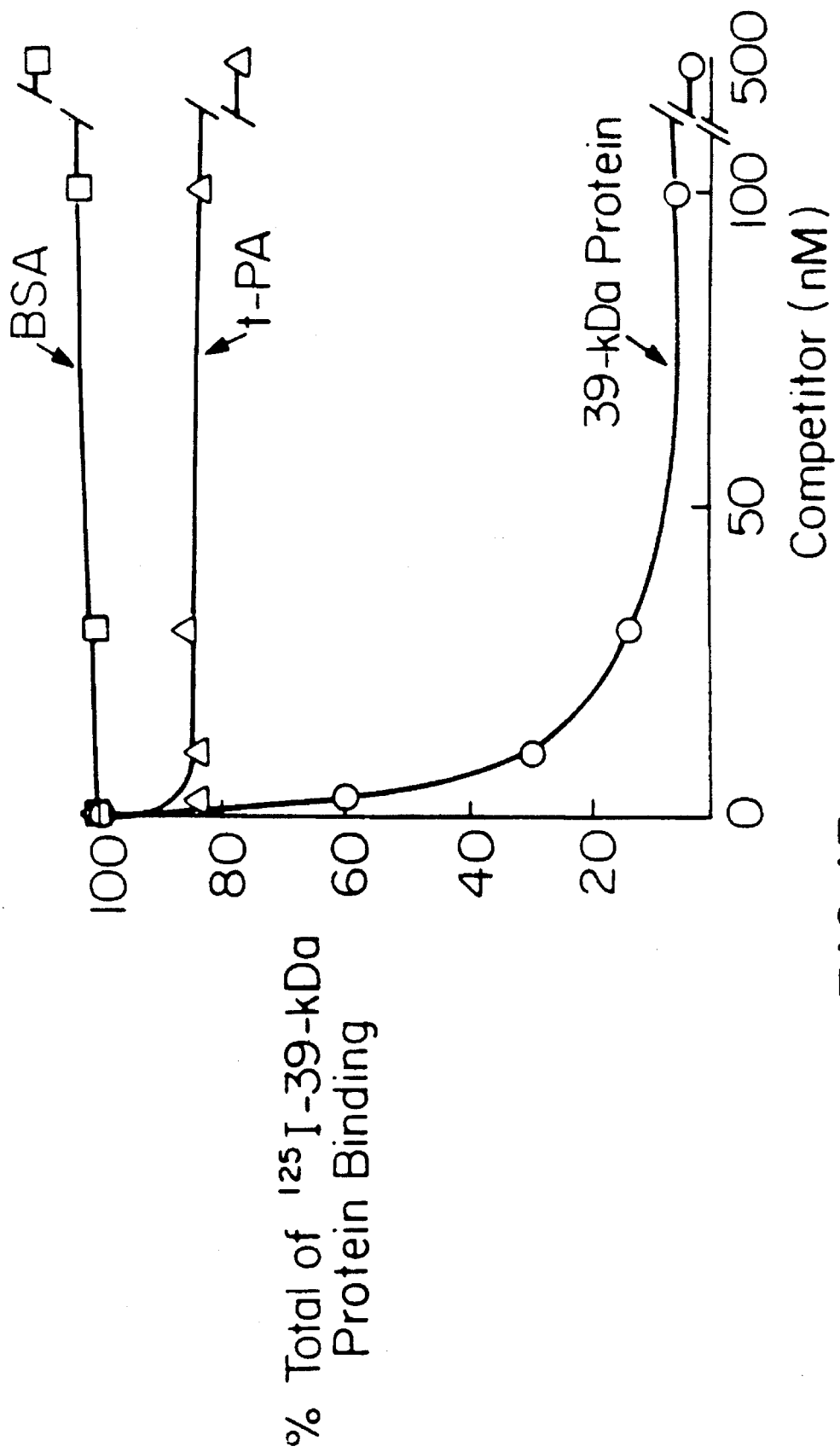

FIG. 13 is a graph of the inhibition of the $^{125}$-39 kDa protein by t-PA. Each symbol represents the average of duplicate determinations and the standard deviations are less than 5%.

Figure 14:
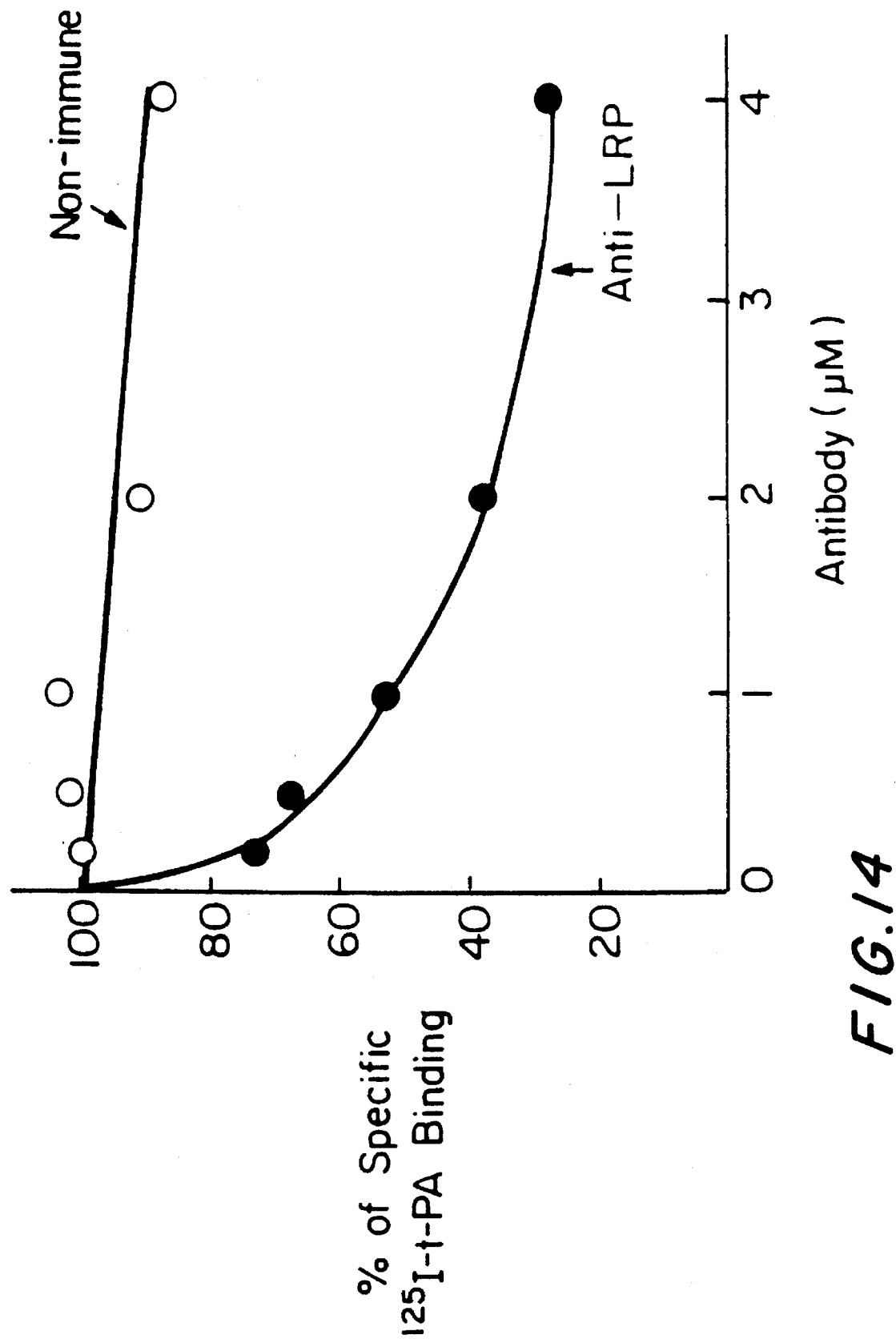

FIG. 14 is a graph of the inhibition of 3 nM $^{125}I$-t-PA binding to HepG2 cells by anti-nRP antibody. (open circles)=rabbit non-immune IgG; (closed circles)=rabbit polyclonal anti-LRP IgG. Each symbol represents the average of duplicate determinations and the standard deviations are less than 5%.

FIG. 15A is a Coomassie-stained SDS-PAGE gel of purified 39 kDa protein (10 μg). FIG. 15B is a graph of the inhibition of $^{125}I$-t-PA binding to rat liver $MH_1C_1$ cells by 39 kDa protein.

FIGS. 16A–B are graphs of the plasma clearance of $^{125}I$-t-PA in rat in vivo in the absence or presence of unlabelled t-PA or 39 kDa protein. Bars=S.E.M. FIG. 16A shows the plasma clearance of $^{125}I$-t-PA alone (n=8) (open circles); the plasma clearance of IMI-t-PA when 12 nmol unlabelled t-PA is administered prior to $^{125}I$-t-PA (n=3) (closed circles); and the plasma clearance of $^{125}I$-t-PA when 250 nmol unlabelled 39 kDa protein is administered prior to $^{125}I$-t-PA (n=4) (closed triangles). FIG. 16B shows the plasma clearance of control proteins $^{125}I$-asialorosomucoid (closed diamonds) and $^{125}I$-orosomucoid (open diamonds).

FIGS. 17A–B is a graph of the plasma clearance of $^{125}I$-39 kDa protein in rat in vivo in the presence of unlabelled 39 kDa protein. (o)=administration of $^{125}I$-39 kDa protein alone (n=6); (●)=administration of 12.5 nmol unlabelled 39 kDa protein prior to $^{125}I$-39 kDa protein (n=4); (■) -administration of 50 nmol unlabelled 39 kDa protein prior to $^{125}I$-39 kDa protein (n=4); (▲)=administration of $^{125}$ nmol unlabelled 39 kDa protein prior to $^{125}I$ -39 kDa protein (n=2).

Figure 18:
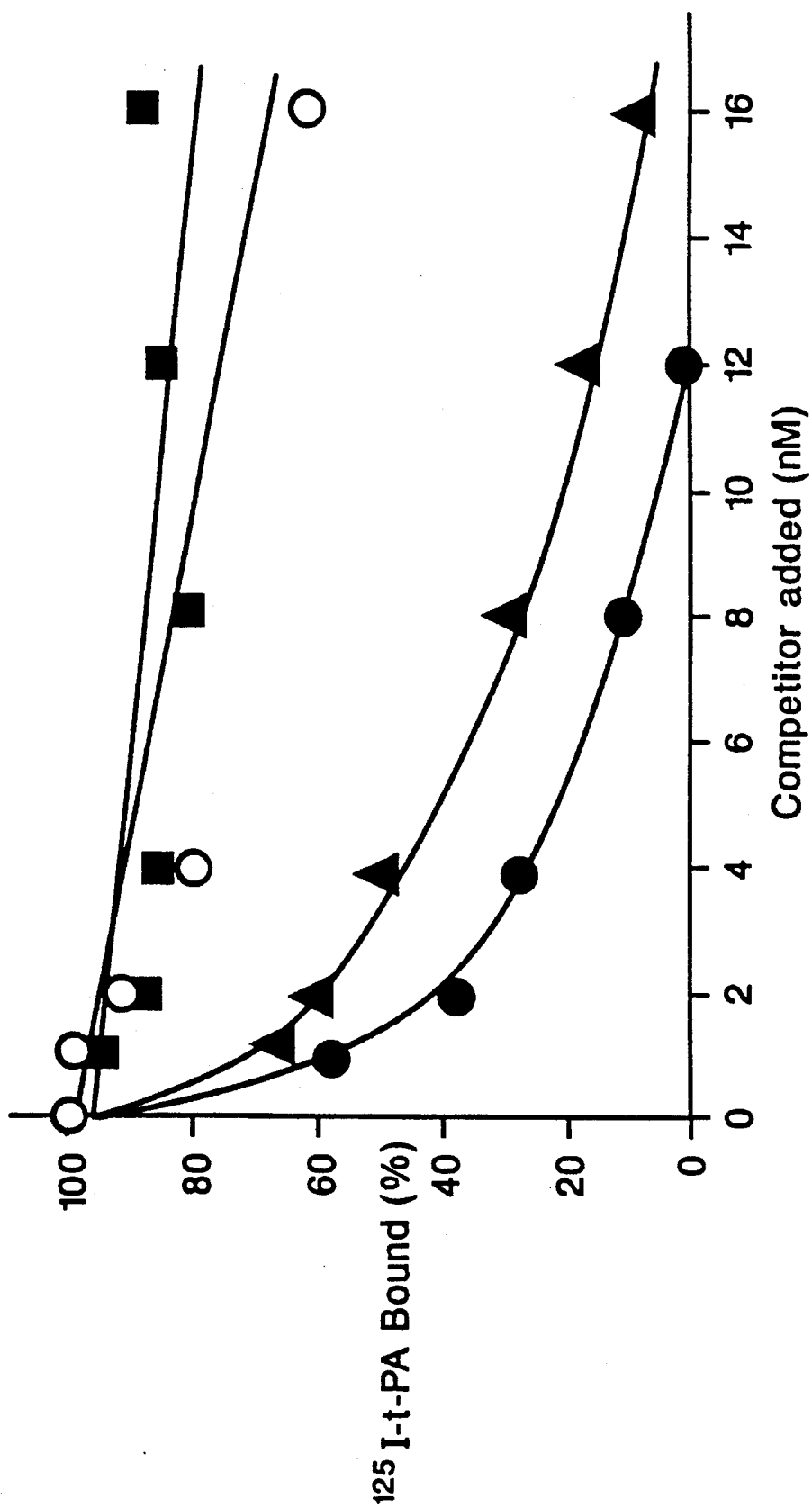

FIG. 18 is a graph of the inhibition of $^{125}I$-t-PA binding to rat liver $MH_1C_1$ cells by intact 39 kDa protein, 20 kDa N-terminal fragment and 28 kDa C-terminal fragment. (●)= intact 39 kDa protein; (■)=the 20 kDa N-terminal fragment; (▲)=the 28 kDa C-terminal fragment; and (o)=PVDF-elution buffer alone.

SUMMARY OF THE INVENTION

The present invention provides a method of inhibiting the hepatic clearance of t-PA in vivo in humans by the administration of a t-PA-hepatic clearance-inhibiting amount of a 39 kDa protein or a t-PA-hepatic clearance-inhibiting fragment thereof. The 39 kDa protein and fragments thereof may be genetically or chemically modified.

An advantage of this method is that the plasma half-life of t-PA is significantly increased.

The present invention also provides a 28 kDa protein and a chemically synthesized gene encoding this protein. It has been found that this 28 kDa protein inhibits hepatic clearance of t-PA.

The present invention also provides a method of thrombolysis in a mammal by the administration of a thrombolytically effective amount of t-PA and a t-PA-hepatic clearance-inhibiting effective amount of 39 kDa protein or a t-PA-hepatic clearance-inhibiting fragment thereof.

An advantage of this method is that the inhibition of hepatic clearance of t-PA enables smaller doses of t-PA to be used to achieve the same level of thrombolysis.

The present invention further provides a pharmaceutical composition for a mammalian patient comprising t-PA and a t-PA-hepatic clearance-inhibiting amount of 39 kDa protein or a t-PA-hepatic clearance-inhibiting fragment thereof.

An advantage of this pharmaceutical composition is that the inclusion of a t-PA-hepatic clearance-inhibiting protein enables a smaller dosage amount of t-PA to be used with both physiological and cost benefits for the patient.

The present invention also provides a composition for treating thrombolytic diseases in a mammal comprising t-PA and a t-PA-hepatic clearance-inhibiting amount of 39 kDa protein or a t-PA-hepatic clearance-inhibiting fragment thereof.

An advantage of this composition is that the amount of t-PA effective for treating thrombolytic diseases is markedly reduced in comparison to current requirements.

Upon further study of the specification and appended claims, further objectives and advantages of this invention will become apparent to those skilled in the art.

DETAILED DESCRIPTION OF THE INVENTION

It is to be understood that while the present invention is primarily contemplated for humans, it is also contemplated for use in veterinary medicine.

In accordance with the invention, a 39 kDa protein which competitively binds the hepatic receptor for t-PA has been found° By binding to the hepatic receptor for t-PA, the 39 kDa protein prevents t-PA from being bound to the receptor and removed from the circulating plasma by endocytosis. This increases the plasma half-life of t-PA thereby prolonging t-PA's therapeutic effectiveness. An increase in the plasma half life of t-PA means that a smaller amount of t-PA may be used, which reduces the risk of systemic fibrinolysis and hemorrhage. As t-PA is very expensive, a significant cost savings can be achieved which, in turn, increases the availability of t-PA for clinical use.

The 39 kDa protein is an active, effective, competitive binding agent for the hepatic receptor for t-PA. This t-PA-hepatic clearance-inhibiting protein is characterized by binding to LRP and inhibiting the binding of t-PA to LRP up to about 80% ($K_i$ of about 0.5 nM) (see Examples 5–8 and 10, infra). Fragments of this 39 kDa protein, particularly a 28 kDa protein fragment, also competitively bind to the t-PA hepatic receptor. When the 39 kDa protein or t-PA-hepatic clearance inhibiting fragment thereof is employed in the present invention, the standard dose of t-PA is reduced up to 90%.

Hepatic clearance of t-PA is inhibited in vivo in humans by administering a t-PA-hepatic clearance-inhibiting amount of the 39 kDa protein or a t-PA-hepatic clearance-inhibiting fragment of the 39 kDa protein. The mode of administration is preferably intravenous. The preferred amount of 39 kDa protein or fragment administered to the human to inhibit hepatic clearance is in the range of about 60 to 6,000 mg/kg of body weight/dose. When the fragment of the 39 kDa protein is the 28 kDa protein, the preferred amount administered to the human to inhibit hepatic clearance is in the range of about 38 to 3,800 mg/kg of body weight/dose. The 39 kDa protein or its fragments may be administered to the human concurrently with t-PA, but is preferably administered up to 20 minutes prior to the administration of t-PA. Administration of the 39 kDa protein or its fragments reduces hepatic clearance of t-PA between 20 and 100%. The reduction in hepatic clearance is measured by the increase in plasma half-life of t-PA.

It is to be understood that modified forms of the 39 kDa protein and fragments thereof which inhibit hepatic clearance of t-PA that are made by chemically or genetically modifying the amino acid sequence of the 39 kDa protein or its fragments are encompassed within the scope of the present invention. Such modified forms are characterized by their ability to bind to LRP and to reduce hepatic clearance of t-PA between 20 and 100%.

The 39 kDa protein of the present invention has the following amino acid sequence set forth in Sequence Listing as SEQ ID NO:1:

```
1           10          20          30
YSREKNQPKPSPKRESGEEFRMEKLNQLWEKAQ
            40          50          60
RLHLPPVRLAELHADLKIQERDELAWKKLKLDG
            70          80          90
LDEDGEKEARLIRNLNVILAKYGLDGKKDARQV
100         110         120         130
TSNSLSGTQEDGLDDPRLEKLWHKAKTSGKFSG
            140         150         160
EELDKLWREFLHHKEKVHEYNVLLETLSTREEI
            170         180         190
HENVISPSDLSDIKGSVLHSRHTELKEKLRSIN
200         210         220         230
QGLDRLRRVSHQGYSTEAEFEEPRVIDLWDLAQ
            240         250         260
SANLTDKELEAFREELKHFEAKIEKHNHYQKQL
            270         280         290
EIAHEKLRHAESVGDGERVSRSREKHALLEGRT
300         310         320
KELGYTVKKHLQDLSGRISRARHNEL
```

The 39 kDa protein was prepared as shown in Example 1.

EXAMPLE 1

Purification of the 39 kDa Protein

The procedure for purification of the 39 kDa protein from strains of *E.coli* carrying the over-expression plasmid pGEX-39 kDa has been described in Herz, J. et al., (1991) J. Biol. Chem. 266, 21232–21238. A modified version of that procedure, described below, was employed.

Cultures of *E.coli* strain DH5α carrying the over-expression plasmid pGEX-39 kDa were grown to mid-log phase in LB medium with 100 μg/ml ampicillin at 37° C. Cultures were cooled to 30° C. and supplemented with 0.01% isopropylthio-β-D-galactoside to induce expression of the glutathione-S-transferase-39 kDa fusion protein. Following a 4–6 hour induction at 30° C., cultures were cooled on ice and collected by centrifugation.

All of the following steps were carried out at 4° C. Cell pellets were lysed in PBSa with 1% Triton X-100, 1 μM pepstatin, 2.5 μg/ml leupeptin, 0.2 mM phenylmethylsulfonyl fluoride (PMSF), and 1 μM ethylenediaminetetraacetate (EDTA). Sonication of this lysate was performed using a Branson Model 450 Sonifier, with the resulting membranes and other cellular debris collected by centrifugation at 15,000 g for 15 minutes. The supernatant from this step was incubated overnight with agarose immobilized glutathione beads (Sigma Chemical Co.) in PBSa and 0.1% sodium azide. The beads were then washed, and elution of the fusion protein was carried out by competition with 5 mM reduced glutathione (Sigma Chemical Co.). Following dialysis, the fusion protein was cleaved by an overnight incubation with 100 ng of activated human thrombin per 50 μg of fusion protein. The glutathione-S-transferase epitope was subsequently removed by further incubation with agarose immobilized glutathione beads.

The 28 kDa protein fragment of the 39 kDa protein ("b28 kDa protein") of the present invention has the following amino acid sequence set forth in the Sequence Listing as SEQ ID NO:2:

```
1                 10                  20
P R L E K L W H K A K T S G K F S G E E L D K L W R 30              40              50
E F L H H K E K V H E Y N V L L E T L S R T E E I H E 60              70              80
N V I S P S D L S D I K G S V L H S R H T E L K E K L R 90                  100
S I N Q G L D R L R R V S H Q G Y S T E A E F E E P R 110             120             130
V I D L W D L A Q S A N L T D K E L E A F R E E L K H 140             150             160
F E A K I E K H N H Y Q K Q L E I A H E K L R H A E S 170             180
V G D G E R V S R S R E K H A L L E G R T K E L G Y T 190             200             209
V K K H L Q D L S G R I S R A R H N E L
```

The 28 kDa protein is characterized by a molecular weight of 28,000 daltons on SDS-PAGE, stability to acid hydrolysis, solubility in 1% Triton X-100, and having approximately the same inhibitory activity ($K_i$) on t-PA binding to the hepatic receptor as the 39 kDa protein. The 28 kDa protein may be cloned and purified as shown in the following example.

EXAMPLE 2

Cloning of the 28 kDa Protein

The 28 kDa protein is produced with a bacterial expression system. The gene encoding this protein is synthesized using polymerase chain reaction (PCR) with the following primers set forth in the Sequence Listing as SEQ ID NO:3 nd SEQ ID NO:4, respectively: 5'CCGCGTGGATC-CCCCAGGCTGGAAAAGCTGTGG3', 5'TCAATGAAT-TCTCAGAGTTCGTTGTGCCGAGCTCT3'. These PCR primers contain built-in restriction sites (BamH1 and EcoR1, respectively). The PCR product after restriction enzyme digestion is cloned directly to the pGEX-2T vector (Pharmacia). Other bacterial expression vectors may be used. The constructed plasmid is used to transform bacteria E.coli strain DH5αF' and this bacterial transformant bearing the recombinant plasmid is used to produce the 28 kDa protein using the procedure of Example 1.

Using standard recombinant techniques, a chemically synthesized gene encoding the 28 kDa protein may be prepared. The chemically synthesized gene comprises a chemically synthesized polynucleotide which codes on expression for the amino acid sequence of the 28 kDa protein given above.

A 28kDa rat protein has also been found which binds to LRP and inhibits binding of t-PA to the LRP hepatic receptor. This rat protein has the following amino acid sequence set forth in the Sequence Listing as SEQ ID NO:5:

```
1          10          20          30
PRLEKLWHKAKTSGISVRLTSCARVLHYKEKIHEY
        40          50          60
NVLLDTLSRAEEGYENLLSPSDMTHIKSDTLAS
        70          80          90
KHSELKDRLRSINQGLDRLRKVSHQLRPATEFE
    100         110         120         130
EPRVIDLWDLAQSANFTEKELESFREELKHFEA
            140         150         160
KIEKHNHYQKQLEISHQKLKHVESIGDPEHISR
            170         180         190
NKEKYVLLEEKTKELGYKVKKHLQDLSSRVSRA
    200
RHNEL
```

Using standard recombinant techniques, a chemically synthesized gene encoding this rat protein may be prepared. The chemically synthesized gene comprises a chemically synthesized polynucleotide which codes on expression for the amino acid sequence of the rat protein given above.

A method of thrombolysis in a mammal is also provided. In accordance with the invention, the method utilizes the t-PA hepatic clearance-inhibiting effect of the 39 kDa protein and fragments thereof. The method comprises administering to the mammal, preferably intravenously, a thrombolytically effective amount of t-PA and a t-PA-hepatic clearance-inhibiting effective amount of the 39 kDa protein or a t-PA-hepatic clearance-inhibiting fragment thereof. The preferred amount of t-PA is between 0.15 and 1.5 mg/kg of body weight/dose. The preferred amount of 39 kDa protein or fragment administered to the mammal is between 60 to 6,000 mg/kg of body weight/dose. When the fragment of the 39 kDa protein is the 28 kDa protein, the preferred amount administered to the mammal is between 38 to 3,800 mg/kg of body weight/dose. The 39 kDa protein or fragment thereof may be administered to the mammal up to 20 minutes prior to administering the t-PA.

A composition for treating thrombolytic diseases which may be employed in the method of thrombolysis includes an effective amount of t-PA and an effective amount of a t-PA hepatic clearance-inhibiting 39 kDa protein or a t-PA hepatic clearance-inhibiting fragment thereof. The t-PA is preferably present in a dosage amount of from about 0.15 to 1.5 mg/kg of body weight/dose. The 39 kDa protein or fragment thereof is present in a dosage amount of from about 60 to 6,000 mg/kg of body weight/dose. When the fragment of the 39 kDa protein is the 28 kDa protein, the dosage amount is from about 38 to 3,800 mg/kg of body weight/dose.

t-PA is primarily used in the treatment of thrombolytic diseases, but t-PA has also been used for treating myocardial infarctions, tumors via fibrinolysis, and sickle cell anemia via fibrinolysis. The present invention accordingly provides a pharmaceutical composition for a mammalian patient containing t-PA, the improvement comprising further including a t-PA hepatic clearance-inhibiting amount of 39 kDa protein or a t-PA hepatic clearance-inhibiting fragment thereof. The t-PA is preferably present in a dosage amount of from about 0.15 to 1.5 mg/kg of body weight/dose. The 39 kDa protein or fragments thereof is present in a dosage amount of from about 60 to 6,000 mg/kg of body weight/dose. When the fragment of the 39 kDa protein is the 28 kDa protein, the dosage amount is from about 38 to 3,800 mg/kg of body weight/dose.

The ability of the 39 kDa protein to bind to the t-PA hepatic receptor is demonstrated in the following examples.

EXAMPLE 3

Specific Binding of the 39 kDa Protein to the MH₁C₁ Cell surface

Rat MH$_1$C$_1$ hepatoma cells are known to specifically bind $^{125}$I-t-PA with high affinity to the cell surface (K$_d$=4.9±1.3 nM (SD); Bmax=78,000±35,000 (SD)) (Bu, G. et al., J. Biol. Chem. 267, 15595–15602). A specific interaction between the 39 kDa protein and rat MH$_1$C$_1$ hepatoma cells was demonstrated by the following saturation binding analyses.

Cell Culture and Media

Rat MH$_1$C$_1$ hepatoma cells were grown in Eagle's minimum essential media (MEM) with Earle's salts (Gibco BRL) supplemented with 10% fetal calf serum, penicillin (100 U/ml), and streptomycin (100 µg/ml) at 37° C. in humidified air containing 5% CO$_2$ as described in Bu, G. et al., (1992) J. Biol. Chem. 267, 15595–15602. Cell monolayers were used at approximately 90% confluence, and the media was replaced the day prior to each experiment.

Radiolabelling of Purified Proteins

Recombinant 39 kDa protein and t-PA were radiolabelled with carrier-free sodium $^{125}$I-iodide (DuPont New England Nuclear Products) using the Iodogen procedure described in Bu, G. et al., (1992) J. Biol. Chem. 267, 15595–15602. Specific radioactivities for each radiolabelled protein were between 1 and 2×10$^7$ cpm/µg of protein as measured by $\gamma$ scintillation spectrometry.

Saturation Binding Analysis

Cells were grown in 12 well dishes to approximately 10$^6$ cells per well. Monolayers were taken directly from 37° C. and cooled on ice. The binding buffer used for the recombinant 39 kDa protein was PBSc (phosphate-buffered saline supplemented with 1 mMCaCl$_2$ and 0.5 mM MgCl$_2$). Each cell monolayer was washed three times with PBSc prior to the addition of binding buffer containing various concentrations of radiolabelled $^{125}$I-39 kDa protein, either in the presence or absence of an excess of unlabelled protein. Cell monolayers were incubated at 4° C. with between 1 and 24 nM recombinant $^{125}$I-39 kDa protein, either in the presence or absence of 0.5 µM unlabelled protein.

Following a 90 minute incubation, cell monolayers were washed three additional times with PBSc to remove nonspecifically associated ligand, and lysed in "low SDS lysis buffer" (0.0625M Tris-HCl, pH 6.8, with 0.2% sodium dodecyl sulfate, 10% glycerol, and 0.01% bromophenol blue), as described in Bu, G. et al., (1992) J. Biol. Chem. 267, 15595–15602. The amount of cell associated ligand was determined by $\gamma$ scintillation spectrometry. In cases where t-PA and the 39 kDa protein were co-bound, the t-PA binding buffer (PBSa containing 0.2 mM CaCl$_2$ and 10 mM ε-amino-n-caproic acid) was used as described in Bu, G. et al., (1992) J. Biol. Chem. 267, 15595–15602.

Figure 1A:
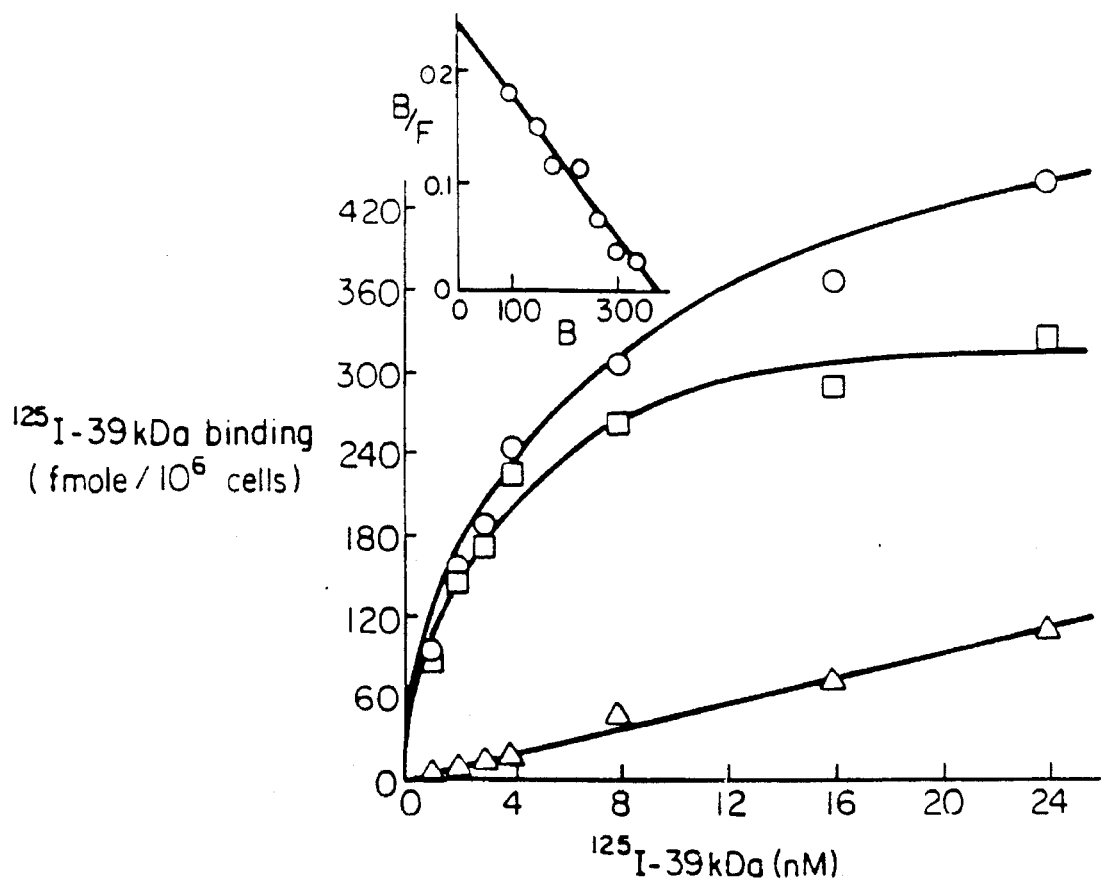
FIG. 1A is a graph of the saturation binding of $^{25l}$I-39 kDa protein to $MH_1C_1$ cells in the presence or absence of 0.5 μM unlabelled 39 kDa protein. (circles)=total ligand binding; (triangles)=non-specific ligand binding. Specific binding (squares) was calculated as the difference between total and non-specific binding. Each symbol represents the mean of triplicate determinations. The inset is a Scatchard plot of specific binding where B=bound $^{125}$I-39 kDa protein and B/F=bound/free $^{125}$I-39 kDa protein.

As shown in FIG. 1A, non-specific binding of $^{125}$I-39 kDa protein increased linearly over the range of concentrations tested, while total binding increased in a curvilinear fashion, approaching an asymptote above 12 nM. Scatchard analysis (23) (inset to FIG. 1A) is consistent with a single homogeneous population of binding sites and yields an equilibrium dissociation constant (K$_d$) of 3.2 nM with 220,000 binding sites per cell, for this particular experiment.

The results from ten independent binding experiments indicate a mean K$_d$ value of 3.3±0.9 (SD) nM for $^{125}$I-39 kDa protein binding to MH$_1$C$_1$ cells, with an average of 380,000±90,000 (SD) binding sites per cell, as shown in the following table, Table 1. A represents the mean values with standard deviations for binding of both the 39 kDa protein and t-PA to MH$_1$C$_1$ cells. The cumulative data from all independent binding experiments was used. B represents the mean values with standard deviation from only simultaneously performed binding experiments. C represents data derived from simultaneous binding experiments performed using either untreated MH$_1$C$_1$ cells, or cells pre-incubated for 30 minutes with 0.1% saponin at 4° C.

TABLE 1

Specific Binding of $^{125}$I-39kDa Protein and $^{125}$I-t-PA to MH$_1$C$_1$ Cells

Figure 1B:
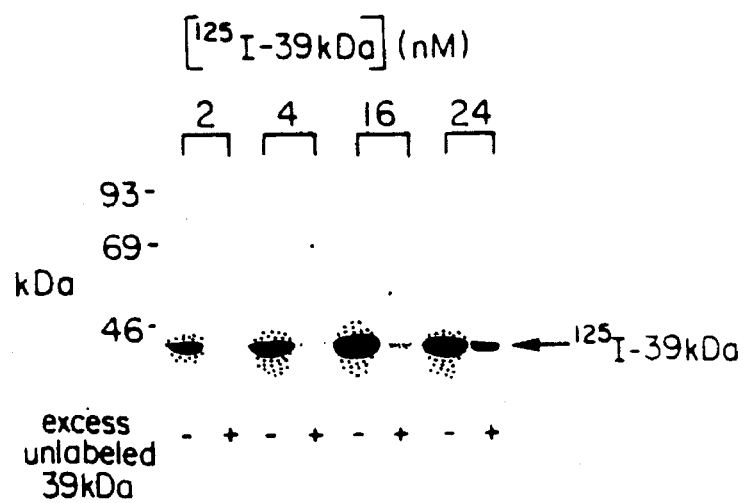
FIG. 1B is a SDS-PAGE gel (10% acrylamide, non-reduced) of equivalent volumes of post-binding cell lysates, each from about 60,000 cells. The position of $^{125}$I-39 kDa protein is indicated by a closed arrow.

| ligand | pre-incubation | Bmax ± S.D. (10³ sites/cell) | Kd ± S.D. (nM) | Experiment (n) |
|---|---|---|---|---|
| A. Summary | | | | |
| $^{125}$I-39kDa | none | 380 ± 190 | 3.3 ± 0.9 | 10 |
| $^{125}$I-t-PA | none | 78 ± 35 | 4.9 ± 1.3 | 7 |
| B. Simultaneous Assays | | | | |
| $^{125}$I-39kDa | none | 390 ± 150 | 3.5 ± 0.9 | 4 |
| $^{125}$I-t-PA | none | 60 ± 35 | 5.6 ± 1.5 | 4 |
| C. Simultaneous Assays Performed in the Presence or Absence of Saponin | | | | |
| $^{125}$I-39kDa | none | 250 ± 8 | 2.7 ± 1.3 | 3 |
| $^{125}$I-t-PA | saponin | 515 ± 24 | 9.1 ± 3.6 | 3 | p These data indicate both specific and saturable binding of the 39 kDa protein to a single kinetic species of high affinity receptor on the MH$_1$C$_1$ cell surface. The nature of the 39 kDa protein binding species was shown by visualizing cell lysates from each binding experiment by sodium dodecyl sulfate polyacrylamide gel electrophoresis (SDS-PAGE) (FIG. 1B). Under the mild conditions used in these experiments (0.2% SDS), the 39 kDa protein appeared to bind in isolation, without apparent association with any auxiliary binding proteins. These experiments demonstrate that there is a specific and saturable interaction between the 39 kDa protein and an MH$_1$C$_1$ cell surface molecule(s).

EXAMPLE 4

Specific Binding of $^{125}$I-t-PA and $^{125}$I-39 kDa Protein to HepG2 Cells The following saturation binding analyses demonstrated that there is a specific interaction between the 39 kDa protein and human hepatoma HepG2 cells. Additionally, the binding parameters to human hepatoma HepG2 cells of $^{125}$I-t-PA and $^{125}$I-39 kDa protein were compared by parallel saturation binding experiments.

Binding studies were carried out at 4° C. to avoid possible ligand uptake and degradation. Binding buffer for $^{125}$I-t-PA included 10 mM EACA since this lysine analog reduced nonspecific $^{125}$I-t-PA binding (presumably to lysine residues on the cell surface) without affecting specific $^{125}$I-t-PA binding. (See, Bu, G. et al., (1992) J. Biol. Chem. 267, 15595–15602). Throughout this example, protein concentration was determined using a Bio-Rad protein assay with bovine serum albumin as a standard. Cell number was determined by counting cells with a hemocytometer.

Cell Culture

Human hepatoma HepG2 cells were maintained in culture as described in (Schwartz, A. L. et al., (1981) J. Biol. Chem.

256, 8878–8881). Cells were cultured in Earle's minimum essential medium (MEM) with glutamine (Gibco Laboratories) supplemented with 10% (v/v) fetal calf serum (Gibco Laboratories), penicillin (100 units/ml), streptomycin (100 μg/ml), and were incubated at 37° C. in humidified air containing 5% $CO_2$. Cultures were supplemented with fresh media 12 hours prior to use. Cell monolayers were generally cultured for two days before use at 80–90% confluence.

Production and Isolation of 39 kDa Protein

The 39 kDa protein was produced and isolated in accordance with the procedure of Example 1.

Protein Iodination

Iodination of t-PA and 39 kDa protein were performed using IODOGEN (Pierce Chemical Co.) as described in Bu, G. et al., (1992) J. Biol. Chem. 267, 15595–15602. The specific activity was generally 5–10 μCi/μg of protein as determined by γ scintillation spectrometry. The unincorporated $^{125}I$ after gel-filtration purification over a PD-10 column (Pharmacia) was less than 2% of the total radioactivity.

Saturation Binding Assays

Cells were seeded into multiwell (12 wells/plate) disposable plastic tissue culture plates 2 days prior to assay. Ligand binding buffer for t-PA was composed of phosphate-buffered saline (PBS) supplemented with 0.2 mM $CaCl_2$ and 10 mM EACA, whereas PBSc (PBS containing 1 mM $CaCl_2$ and 0.5 mM $MgCl_2$) was used for 39 kDa protein binding. Binding experiments were performed at 4° C. to prevent possible concomitant internalization during the binding interval. Cell monolayers were washed three times on ice with prechilled binding buffer. Binding was initiated by adding 0.5 ml binding buffer containing selected concentrations of $^{125}I$-labelled ligand in the absence or presence of an excess unlabelled ligand (1 μM). After incubation at 4° C. for 1.5 hours, buffer containing unbound ligand was removed. Cells were then washed three times with binding buffer and lysed in 0.0625M Tris-HCl, pH 6.8, containing 0.2% (w/v) SDS and 10% (v/v) glycerol ("low-SDS lysis buffer"). Radioactivity of cell lysates was quantified by γ scintillation spectrometry. For some experiments, cell lysates were further analyzed by SDS-PAGE and autoradiography as described below. Total binding was determined in the presence of $^{125}I$-labelled ligand alone. Nonspecific binding was determined in the presence of excess unlabelled ligand. Specific ligand binding was defined as the difference between total and nonspecific binding.

Figures 2A, 2B:
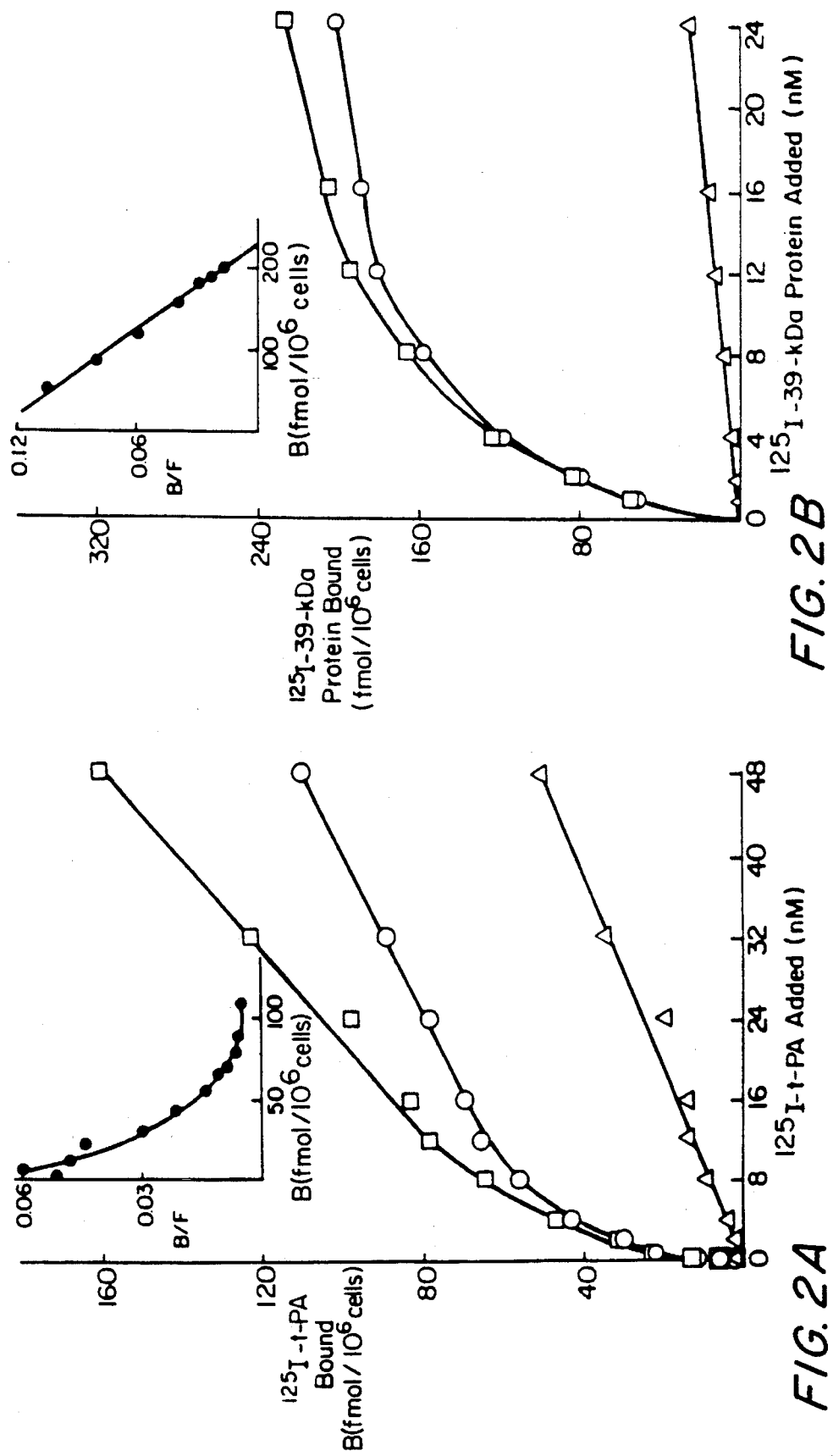
FIGS. 2A–B are graphs of the saturation binding of $^{125}$I-t-PA and $^{125l}$-39 kDa protein to HepG2 cells.
Figure 3A:
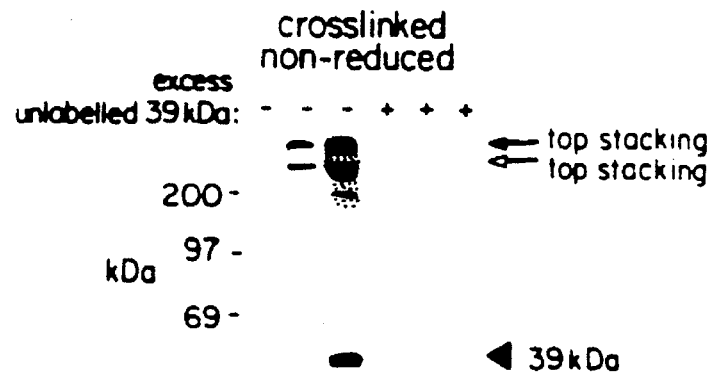
FIGS. 3A–D are SDS-PAGE gels (8.5% acrylamide) of specific cross-linking of $^{125}$I-39 kDa protein to low density lipoprotein receptor-related protein (LRP) in the presence and absence of 0.5 μM unlabelled 39 kDa protein.
Figure 3B:
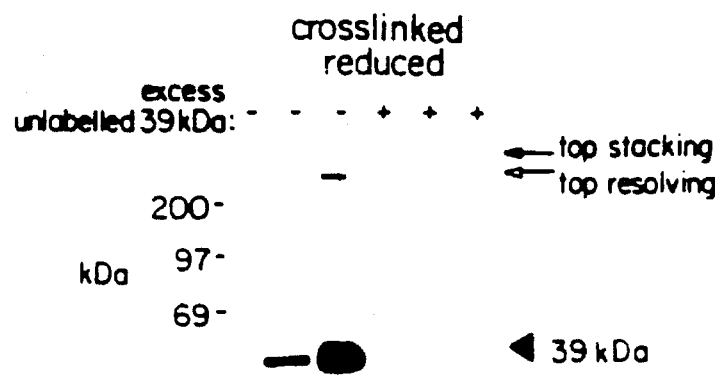
Figure 3C:
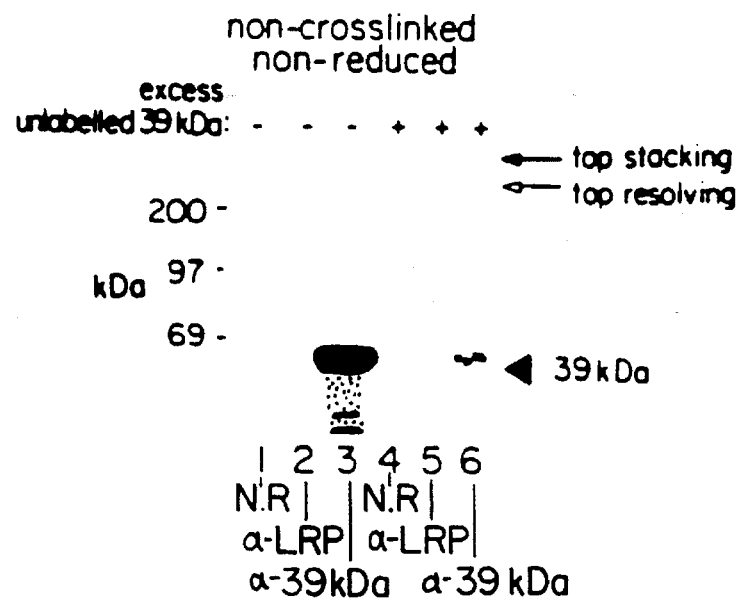
Figure 3D:
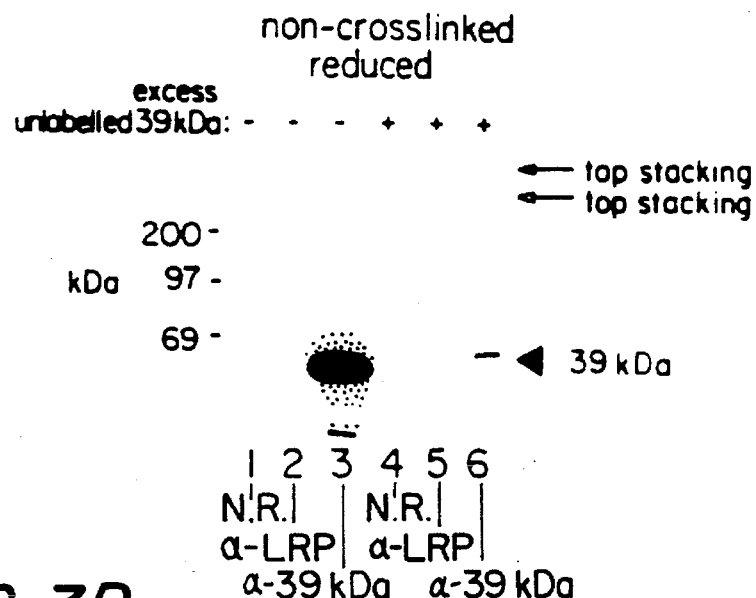

Specific binding of $^{125}I$-t-PA over the concentration range of 0.1–48 nM yielded a curvilinear plot. FIG. 2A shows a representative experiment from seven such experiments performed. Scatchard analysis of the binding data showed a curvilinear plot concave upwards (inset, FIG. 2A). This result may be due to either the presence of multiple classes of binding sites with different but fixed affinities, or the existence of site-site interactions of the type defined as "negative cooperativity". (See Meyts, P. D. et al., (1976) J. Biol. Chem. 251, 1877–1888). Due to the type of saturation binding experiments performed, these two possibilities could not be distinguished. When multiple classes of binding sites are assumed, an estimate of two binding sites best fit the data. From the Scatchard analysis shown in FIG. 2A, 40,300 sites are estimated for the high affinity binding ($K_d$=1.6 nM) and 146,200 sites ($K_d$=32.5 nM) for the low affinity binding. When cell lysates from selected ligand concentrations were analyzed via SDS-PAGE, specific binding occurred predominantly in the form of the $^{125}I$-t-PA:PAI-1 complex. This is consistent with PAI-1-dependent $^{125}I$-t-PA binding on HepG2 cells. (See, Morton, P. A. et al., (1989) J. Biol. Chem. 264, 7228–7235; Bu, G. et al., (1992) J. Biol. Chem. 267, 15595–15602).

Specific binding of $^{125}I$-39 kDa protein to HepG2 cells was performed over the concentration range of 1–24 nM. As shown in FIG. 2B, the 39 kDa protein specifically bound to HepG2 cells with a low level of non-specific binding. Saturation of specific binding was observed at $^{125}I$-39 kDa protein concentrations in excess of 12 nM. Scatchard analysis of the binding data from five such experiments yielded 197,000±23,000 (S.D.) homogeneous high affinity surface binding sites per cell with an apparent $K_d$=5.1±0.8 nM (S.D.) (166,000 binding sites per cell and $K_d$=4.9 nM for the experiment shown in FIG. 2B). When post-binding cell lysates were analyzed by SDS-PAGE, $^{125}I$-39 kDa protein was observed at its native molecular mass (i.e., 39 kDa) indicating that the binding did not include an SDS-stable complex with other proteins.

The following example demonstrates that low density lipoprotein receptor related protein (LRP) is a receptor for the 39 kDa protein.

EXAMPLE 5

Cross-linking of $^{125}I$-39 kDa Protein to the $MH_1C_1$ Cell Surface

The 39 kDa protein was originally isolated via its ability to co-purify with a low density lipoprotein receptor related protein (LRP) by α2-macroglobulin affinity chromatography. See Ashcom, J. D. et al., (1990) J. Cell Biol. 110, 1041–1048; Jensen, P. H. et al., (1989) FEBS Lett. 255, 275–280. This low density lipoprotein receptor-related protein (LRP) with a molecular mass of >500 kDa has recently been identified and characterized as a new member of the LDL receptor family (Herz, J. et al., (1988) EMBO J. 7, 4119–4127; Beisiegel, U. et al., (1989) Nature 341, 162–164, Brown, M. S. et al., (1991) Curr. Opin. Lipidol. 2, 65–72). This plasma membrane receptor is unique not only because of its large molecular size but also because of its multifunctional nature in ligand recognition. Studies have shown that LRP mediates binding and endocytosis of both apoprotein E-enriched B-migrating very low density lipoprotein (B-VLDL) (Beisiegel, U. et al., (1989) Nature 341, 162–164; Lund, H. et al., (1989) Proco Natl. Acad. Sci. USA 9318–9322) and protease- or methylamine-activated $α_2$-macroglobulin ($α_2M$) (Strickland, D. K. et al., (1990) J. Biol. Chem. 265, 17401–17404). Based on the following cross-linking studies, it was found that LRP functions as a $MHiC_1$ cell specific 39 kDa protein receptor.

Metabolic Labelling

Cells were grown in 10 cm dishes as described above in Example 3. Cell monolayers were washed three times with pre-warmed Eagle's minimum essential media (MEM) with Earle's salts lacking L-methionine (Washington University Center for Basic Cancer Research). Following two 15 minute pre-incubations at 37° C. with this same media, cells were labelled by the addition of methionine deficient MEM containing 0.4 mCi/ml $^{35}S$-methionine (Amersham Corp.). Labelling was carried out for 4–5 hours at 37° C. After metabolic labelling, cell monolayers were cooled on ice, washed three times with cold PBSc, and incubated with 14 nM of the radiolabelled $^{125}$I-recombinant 39 kDa protein of Example 3, either in the presence or absence of an excess of unlabelled 39 kDa protein, to allow specific binding to the cell surface receptor.

Chemical Cross-Linking

Saturation binding was performed as described above, but with 10 cm dishes of MHiCl cells. Either unlabelled or $^{35}$S-methionine labelled cells were used. Following incubation with radiolabelled and unlabelled ligands (39 kDa proteins), cell monolayers were washed three times with PBSc to remove nonspecifically associated ligand and incubated with either PBSc alone or PBSc containing 0.5–1 mM dithiobis-(sulfosuccinnimidylpropionate) (DTSSP) (Pierce Chemical Co.), a disulfide bond containing, thiocleavable cross-linker. After one hour, cross-linking reactions were quenched by three washes with tris-buffered saline, and cell monolayers were solubilized in PBSa containing 1% Triton X-100 and 1 mM PMSF. Immunoprecipitations were performed as described below.

Immunoprecipitation

Aliquots of cell lysates from cross-linking and metabolic labelling experiments were added to equal volumes of PBSc containing 1% Triton X-100, 0.5% sodium deoxycholate, 1% sodium dodecyl sulfate (SDS), 0.5% bovine serum albumin, and 1mM PMSF (immunomix). When metabolically labelled cells were used, lysates were first pre-cleared by an overnight incubation with rabbit pre-immune serum and a subsequent incubation with an excess of protein-A beads (Repligen). Samples were then immunoprecipitated with 0.6 μg of affinity purified α-39 kDa antibody or affinity purified rabbit α-human LRP antibody (American Red Cross, Rockville, Md.). Affinity purified α-39 kDa antibody was prepared in New Zealand white rabbits following injection of purified recombinant 39 kDa protein in accordance with the procedure described in Schwartz, A.L. et al., (1983) J. Biol. Chem. 258, 11249–11255.

When unlabelled cells were cross-linked to a single radiolabelled ligand, no pre-immune clearance of cell lysates was necessary, and either α-LRP immune serum or α-39 kDa protein immune serum was substituted for the affinity purified antibody. In some cases, samples of cell lysates were also immunoprecipitated with 30 ml of immune α-t-PA serum. Following each immunoprecipitation, bead samples were split in half and boiled in 0.0625M Tris-HCl, pH 6.8, 2% SDS, and 10% glycerol as described in Laemmli, U.K., (1970) Nature 227, 680–685, either in the presence or absence of 5% 2-mercaptoethanol. Samples were then separated by sodium dodecyl sulfate polyacrylamide gel electrophoresis (SDS-PAGE), with the gels subsequently fixed and vacuum dried. Autoradiography was performed at −70° C. with Hyperfilm-MP autoradiography film (Amersham Corp.).

FIG. 3 shows the results from a typical experiment. Under conditions where no cross-linker was used (FIGS. 3C and D), a single band corresponding to the 39 kDa protein (arrowhead) was immunoprecipitated only with α-39 kDa serum. Samples electrophoresed under either reducing or non-reducing conditions show that the α-LRP antibody was unable to immunoprecipitate the radiolabelled 39 kDa ligand in the absence of cross-linker. Since there was a marked decrease in the amount of $^{125}$I-39 kDa protein bound in the presence of an excess of unlabelled protein, the association of ligand with its cell surface receptor was shown to be specific. In FIGS. 3A and 3B, the radiolabelled 39 kDa protein was both bound and cross-linked to the $MH_1C_1$ cell surface. When samples from each immunoprecipitation were analyzed under non-reducing conditions (FIG. 3A), the complex of ligand associated radioactivity was immunoprecipitable with both α-LRP and α-39 kDa antibodies. This complex was of very high apparent molecular weight, remaining largely in the stacking gel during electrophoresis (arrows). Again, this interaction was shown to be specific, as the association of $^{125}$I-39 kDa with this high molecular weight complex was abrogated in the presence of an excess of unlabelled 39 kDa protein. When these same samples were electrophoresed in the presence of 5% 2-mercaptoethanol to dissociate the cross-linker (FIG. 3B), a single 39 kDa binding species was seen.

The foregoing experiments demonstrate that there is a specific interaction between the 39 kDa protein and the $MH_1C_1$ cell surface which is mediated, at least in part, by an association with LRP.

EXAMPLE 6

Chemical Cross-linking of t-PA:PAI-1 Complex to LRP on HepG2 Cells

Studies by Orth, K. et al., (1992) Proc. Natl. Acad. Sci. USA 89, 7422–7426, demonstrated via ligand blotting the binding of t-PA:PAI-1 complexes to isolated LRP immobilized on gels. Endocytosis by LRP and subsequent degradation of t-PA:PAI- 1 complexes was also observed in simian COS tumor cells, a non-hepatocyte cell line. The following experiment showed that a direct interaction between the t-PA:PAI-1 complex and LRP in human hepatocytes occurs based on chemical cross-linking following ligand binding to human hepatoma HepG2 cells. In accordance with the present invention, it was hypothesized that binding and subsequent cross-linking of the t-PA:PAI-1 complex to LRP on HepG2 cells should yield a trimeric complex, t-PA:PAI-1-LRP. Therefore, if one component in this trimeric complex is radiolabelled, antibodies to the other components should be able to immunoprecipitate the radiolabelled protein. A thio-cleavable, water-soluble, and membrane-impermeant reagent DTSSP was used as the cross-Linker, as described in Bu, Go et al., (1992) J. Biol. Chem. 267, 15595–15602; and Bu, G. et al., (1992) Proc. Natl. Acad. Sci. USA 89, 7427–7431. Following ligand binding and cross-linking, cell lysates were used for immunoprecipitation with various antibodies, in order to characterize the nature of the cross-linked protein complexes. Chemical cross-linking experiments were performed with either $^{125}$I-t-PA cross-linked to unlabelled HepG2 cells, or unlabelled t-PA cross-linked to $^{35}$S-methionine metabolically-labelled HepG2 cells. Throughout this example, protein concentration was determined using a Bio-Rad protein assay with bovine serum albumin as a standard. Cell number was determined by counting cells with a hemocytometer.

Metabolic Labelling

Cells growing in 10 cm dishes at about 80% confluence were incubated for 30 min at 37° C. in two changes of Earle's minimum essential medium lacking L-methionine and containing 2 mM L-glutamine (Gibco Laboratories). Metabolic labelling was initiated by the addition of the above medium supplemented with $^{35}$S-methionine (400 μCi/ ml)(Amersham). Following incubation for 5 hours at 37° C., cell monolayers were washed with binding buffer and were used for ligand binding and chemical cross-linking experiments as described below.

Chemical Cross-linking

Experiments were performed with either $^{125}$I-labelled ligand cross-linked to unlabelled cells or unlabelled ligand cross-linked to $^{35}$S-methionine metabolically-labelled cells. After ligand binding at 4° C., each cell monolayer was washed three times with PBSc. Chemical cross-linking was performed by incubating the cell monolayer with PBSc containing 0.5 mM dithiobis(sulfosuccinnimidylpropionate) (DTSSP) (Pierce Chemical Co.). After 30 min at 4° C., the reaction was quenched by washing the cell monolayer two times with Tris-buffered saline (TBS). Cells were then solubilized in PBSc containing 1% (v/v) Triton X-100 (Sigma Chemical Co.) and 1 mM phenylmethylsulfonyl fluoride (PMSF) (Sigma Chemical Co.) ("lysis buffer") for 30 min at 4° C. with a brief sonication at low power output and occasional vortexing. These solubilized cell lysates were subsequently used for immunoprecipitation.

Antibodies

All antibodies used in these studies were rabbit polyclonal antibodies. Anti-t-PA, anti-PAI-1, and anti-39 kDa protein antibodies were produced using recombinant proteins. Anti-LRP antibody was generated against purified human placental LRP provided by Dudley K. Strickland (American Red Cross, Rockville, Maryland). Total IgG for each antibody was purified using Protein A-agarose. Specific IgG for each antibody was affinity-purified against its corresponding protein coupled to CNBr-activated Sepharose 4B (Pharmacia).

Immunoprecipitation

Each cell lysate from chemical cross-linking experiments was divided into equal portions depending upon the number of antibodies used. Each aliquot of the cell lysate was then brought to 0.5 ml with lysis buffer and was mixed with 0.5 ml of PBSc containing 1% (v/v) Triton X-100 (Sigma Chemical Co.), 0.5% (w/v) sodium deoxycholate (Sigma Chemical Co.), 1% (w/v) SDS, 0.5% (w/v) bovine serum albumin (Sigma Chemical Co.), and 1 mM PMSF (Sigma Chemical Co.) ("immunomix"). SDS was included in the immunomix to reduce non-specific immunoprecipitation. Primary antibody (10 µl normal rabbit serum (Sigma Chemical Co.), or 1 µg affinity-purified IgG) was added, and the samples were rocked overnight at 4° C. followed by incubation for 1 hour at room temperature with 50 µl of protein A-agarose (Repligen). Non-bound radioactivity was removed by washing protein A-agarose beads three times with immunomix and three times with PBSc. The protein A-agarose beads were divided into two equal parts before the final wash for nonreducing and reducing assays. The immunoprecipitated material was then released from the beads by boiling each sample for 5 min in 0.0625M Tris-HCl, pH 6.8, 2% (w/v) SDS, and 10% (v/v) glycerol ("Laemmli sample buffer") (Laemmli, U. K., (1970) Nature 227, 680–685) with or without 5% (v/v) 2-mercaptoethanol, and was analyzed by SDS-PAGE as described below.

SDS-PAGE and Autoradiograph

Samples of cell lysates or immunoprecipitations were analyzed by SDS-PAGE using polyacrylamide slab gels as described in Laemmli, U. K., (1970) Nature 227, 680–685, under reducing or non-reducing conditions. The following pre-stained molecular weight standards from Bio-Rad were used: myosin: 205 kDa; β-galactosidase: 117 kDa; bovine serum albumin: 80 kDa; ovalbumin: 50 kDa. Autoradiography of $^{125}$I-labelled proteins was performed with dried polyacrylamide gels using Hyperfilm-MP (Amersham). For fluorography of $^{35}$S-labelled proteins, gels were impregnated with Amplify (Amersham), dried, and exposed to films. Films were placed at −70° C. for various periods of time as specified in each figure prior to developing.

Figure 4A:
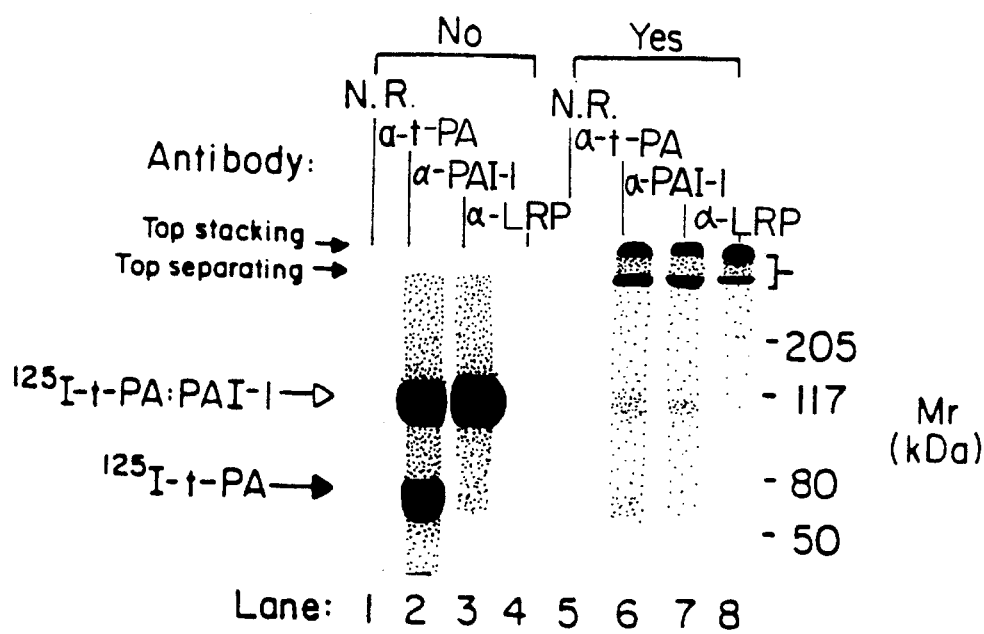
FIGS. 4A–B are SDS-PAGE gels of chemical cross-linking of $^{125}$I-t-PA:PAI-1 to LRP on HepG2 cells. (N.R.)= normal rabbit serum; (α-t-PA)=anti-t-PA antibody; (α-PAI-1)=anti-PAI-1 antibody; (α-LRP)=anti-LRP antibody.
Figure 4B:

FIG. 4 shows an experiment with $^{125}$I-t-PA binding and cross-linking to HepG2 cells. Cell lysates without or with cross-linking were immunoprecipitated with one of the following antibodies: normal rabbit serum, anti-t-PA antibody, anti-PAI-1 antibody, or anti-LRP antibody. The immunoprecipitated material was then analyzed by SDS-PAGE under nonreducing (FIG. 4A) or reducing (FIG. 4B) conditions. Under nonreducing conditions and without cross-linking, the $^{125}$I-t-PA:PAI-1 complex was immunoprecipitated by both anti-t-PA (lane 2) and anti-PAI-1 antibody (lane 3) confirming the PAI-1-dependent n$^{125}$I-t-PA binding to HepG2 cells with the $^{125}$I-t-PA:PAI-1 complex being the vast majority of the bound ligand. Uncomplexed $^{125}$I-t-PA was observed with anti-t-PA antibody (lane 2) but not with anti-PAI-1 antibody (lane 3). The appearance of the uncomplexed $^{125}$I-t-PA (about 40% of the total cell-associated ligand radioactivity) in post-binding lysates was predominantly due to dissociation of $^{125}$I-t-PA and PAI-1 during immunoprecipitation and washing with the immunomix containing 1% SDS and 1% Triton X-100. When the cell lysates were analyzed directly using low-SDS sample buffer without prior immunoprecipitation, more than 90% of the specific binding species was in the form of $^{125}$I-t-PA:PAI-1 complex as appears in FIG. 5B (data not shown). In the absence of cross-linking, anti-LRP antibody did not immunoprecipitate any $^{125}$I-labelled ligand (lane 4) indicating that this antibody does not have any cross-reactivity with the $^{125}$I-t-PA:PAI-1 complex. However, with chemical cross-linking, anti-LRP antibody (lane 8), in addition to anti-t-PA antibody (lane 6) and anti-PAI-1 antibody (lane 7), immunoprecipitated $^{125}$I-labelled ligands. Since anti-LRP antibody does not cross-react with the $^{125}$I-t-PA:PAI- 1 complex (lane 4), this specific immunoprecipitation by anti-LRP antibody must be a result of the $^{125}$I-t-PA:PAI-1 complexes cross-linked to LRP. The ligand-receptor complexes consisting of $^{125}$I-t-PA:PAI-1 and LRP appeared as a broad smear migrating on top of a 7% SDS-polyacrylamide gel with a molecular mass estimated to be greater than 600 kDa. However, when the same material was analyzed by SDS-PAGE under reducing conditions, the radioligand $^{125}$I-t-PA:PAI-1 complex and $^{125}$I-t-PA appeared following reduction of the thiocleavable cross-linker DTSSP (FIG. 4B). Reduction of the cross-linked material caused additional dissociation of the $^{125}$I-t-PA:PAI-1 complex resulting in an even greater amount of free $^{125}$I-t-PA. Normal rabbit serum showed no specific interaction with any of the cross-linked material (lanes 1 and 5).

Figure 6:
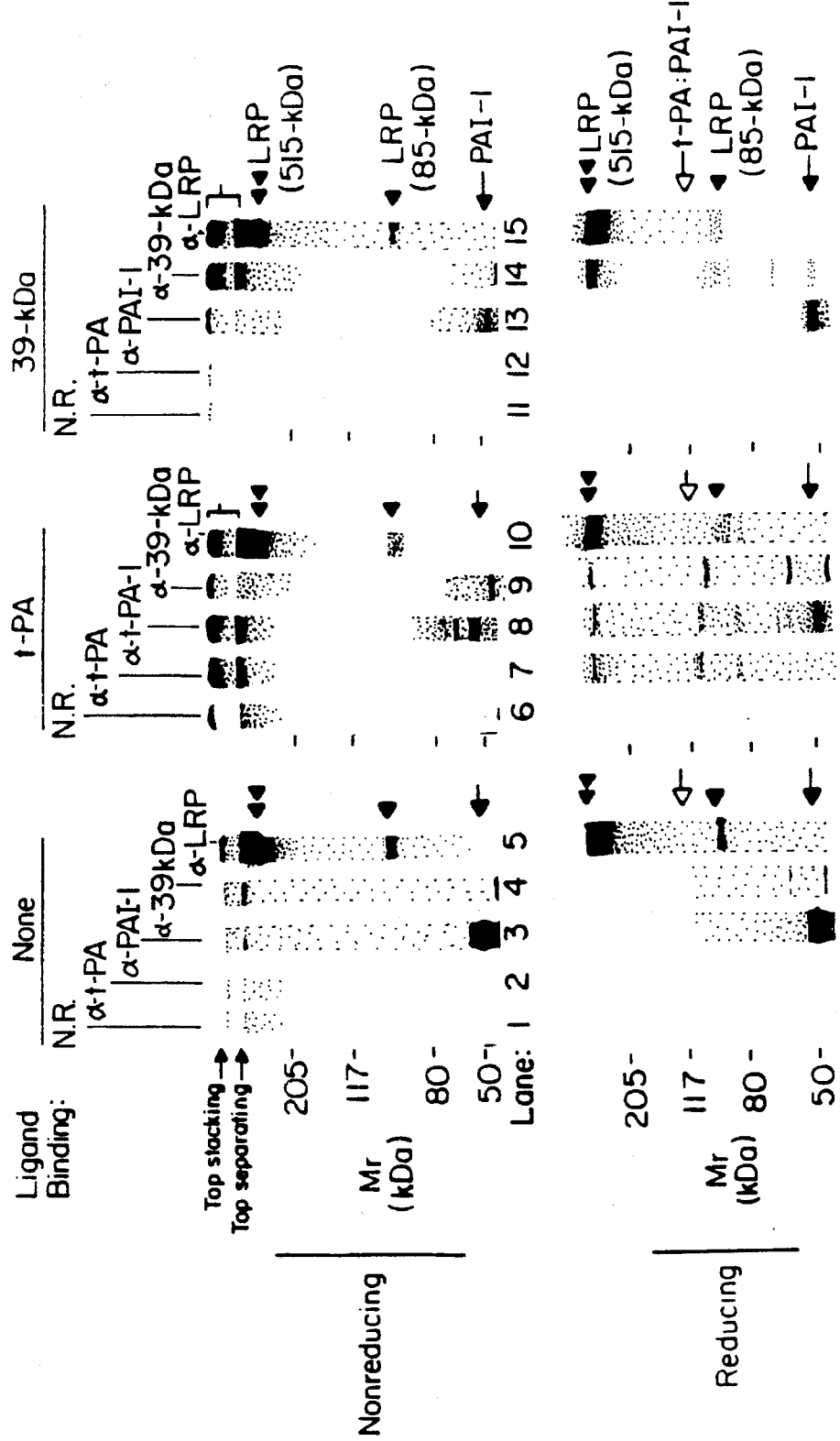
FIG. 6 are SDS-PAGE gels of chemical cross-linking of t-PA:PAI-1 to LRP on $^{35}$S-methionine-labelled HepG2 cells which were analyzed under nonreducing or reducing conditions. (N.R.)=normal rabbit serum (lanes 1, 6, 11); (α-t-PA)=anti-t-PA antibody (lanes 2, 7, 1.2); (α-PAI-1)=anti-PAI-1 antibody (lanes 3, 8, 13); (α-39 kDa)=anti-39 kDa protein antibody (lanes 4, 9, 14); (α-LRP)=anti-LRP antibody (lanes 5, 10, 15). The regions of cross-linked material in the non-reducing gel are marked with brackets. The following positions are indicated: LRP large subunit (515 kDa) (2 closed arrowheads); LRP small subunit (85 kDa) (1 closed arrowhead); PAI-1 (1 closed arrow); and t-PA:PAI-1 complex (1 open arrow).

To exclude the possibility that chemical cross-linking of $^{125}$I-t-PA:PAI-1 to HepG2 cells generated an antigenic epitope for anti-LRP antibody, unlabelled t-PA was cross-linked to $^{35}$S-methionine metabolically-labelled HepG2 cells. This approach allowed direct visualization of the binding protein for the t-PA:PAI-1 complex or the 39 kDa protein and the determination of its relationship to LRP. Following $^{35}$S-methionine metabolic labeling of HepG2 cells, cell monolayers were incubated with binding buffer alone, or binding buffer containing t-PA (15 nM) or the 39 kDa protein (15 nM) (FIG. 6). Cell monolayers in the absence of ligand was lysed directly without chemical cross-linking whereas those following ligand binding were subjected to chemical cross-linking with DTSSP. Each of the cell lysate preparations was then immunoprecipitated with one of the following antibodies: normal rabbit serum (lanes 1, 6, 11), anti-t-PA antibody (lanes 2, 7, 12), anti-PAI-1 antibody (lanes 3, 8, 13), anti-39 kDa protein antibody (lanes 4, 9, 14), or anti-nRP antibody (lanes 5, 10, 15). The immunoprecipitated materials were then analyzed by 7% SDS-PAGE under either nonreducing or reducing conditions.

As shown in FIG. 6, anti-PAI-1 antibody immunoprecipitated PAI-1 from all the HepG2 cell lysates consistent with the well recognized production of PAI-1 by HepG2 hepatoma cells. (See, Bugelski, P. J. et al., (1989) Thromb. Res. 53, 287–303; Owensby, D. A. et al., (1991) J. Biol. Chem. 266, 4334–4340; Bu, G. et al., (1992) J. Biol. Chem. 267, 15595–15602; Sprengers, E. D. et al., (1985) J. Lab Clin. Med. 105, 751–758). When an $^{35}$S-methionine-labelled HepG2 monolayer was analyzed without incubation with either t-PA or 39 kDa protein, only the anti-LRP antibody was able to immunoprecipitate the two LRP subunits (515 kDa and 85 kDa) (lanes 5). However, following binding of unlabelled t-PA and chemical cross-linking, the $^{35}$S-labelled ligand-receptor complexes were immunoprecipitable not only by anti-LRP antibody (lanes 10) but also by anti-t-PA antibody (lanes 7) and anti-PAI-1 antibody (lanes 8). When these materials were analyzed under reducing conditions, the LRP subunits, as well as the t-PA:PAI-1 complexes were observed. These results are thus consistent with the nature of the high molecular weight receptor-ligand complexes composed of the t-PA:PAI-1 complex (ligand) and LRP (receptor). Radiolabelling of the t-PA:PAI-1 complex was a result of complex formation between unlabelled t-PA and endogenous $^{35}$S-methionine-labelled PAI-1.

When the $^{35}$S-methionine-labelled HepG2 cell monolayer was exposed to externally added 39 kDa protein, the $^{35}$S-methionine-labelled ligand-receptor complex appearing on top of the gel was immunoprecipable not only by anti-LRP antibody (lanes 15), but also by anti-39 kDa protein antibody (lanes 14). Analysis of these cross-linked materials under reducing conditions yielded the 515 kDa radiolabelled. LRP band when immunoprecipitated with anti-39 kDa antibody, further demonstrating the receptor protein for 39 kDa protein on HepG2 cells is LRP.

EXAMPLE 7

The 39 kDa Protein is Cross-linked Predominately to LRP on the $MH_1C_1$ Cell Surface It was found that LRP is the predominant 39 kDa protein binding species by cross-linking unlabelled 39 kDa protein to the surface of radiolabelled $MH_1C_1$ cells using the procedures of Example 5 with the following modifications. Labelling was carried out at 37° C. for 4–5 hours in methionine deficient Earle's MEM media supplemented to 0.4 mCi/ml with $^{35}$S-methionine (Amersham Corp.). Following several washes, labelled monolayers were bound with unlabelled 39 kDa protein,:and either cross-linked by the addition of 0.5 mMDTSSP, or incubated in PBSc alone. Lysis and immunoprecipitation were carried out as described above in

EXAMPLE 5

FIG. 7 shows the results from a typical experiment. When radiolabelled $MH_1C_1$ cells were cross-linked to unlabelled 39 kDa protein, a complex of very high apparent molecular weight resulted, which was immunoprecipitable with both the α-39 kDa and, to a lesser degree, the α-human LRP affinity purified antibodies (FIG. 7A, lanes 4–6). Antibodies to human LRP were used as no α-rat LRP affinity purified antibody is presently available. This high molecular weight complex was electrophoretically identical to that seen when radiolabelled $^{125}$I-39 kDa protein was cross-linked to unlabelled $MH_1C_1$ cells (compare with FIG. 3A, lanes 2 and 3). In addition to the cross-linked complex, uncross-linked endogenously labelled 39 kDa protein (lane 5, arrowhead), and both the 520 kDa (closed arrow and 85 kDa (open arrow) subunits of the LRP receptor were visible. When these same immunoprecipitations were electrophoresed in the presence of the reducing agent 2-mercaptoethanol, the cross-linker was cleaved, and the cross-linked complex was dissociated into its component peptides (FIG. 7B, lanes 4–6). In both cases, the cross-linked complex was shown to contain almost exclusively the 520 kDa subunit, and to a lesser degree, the 85 kDa subunit of the LRP receptor. In lanes resulting from immunoprecipitation with the α-human LRP antibody, less of the high molecular weight cross-linked complex was evident. It is believed that this occurs partly because the recognition epitopes for the α-LRP antibody are obscured by binding of the 39 kDa protein.

When metabolically labelled cell lysates which have been bound with, but not cross-linked to, unlabelled 39 kDa protein were immunoprecipitated with the α-39 kDa antibody, only endogenously labelled 39 kDa protein was seen (arrowhead). No high molecular weight complex was evident. Also, in the absence of cross-linker, immunoprecipitation of metabolically labelled cell lysates with α-human LRP antibodies results in only the 520 kDa (closed arrow) and the 85 kDa (open arrow) subunits of the LRP receptor. Again, no high molecular weight complex was evident. Samples electrophoresed under both reducing and non-reducing conditions gave similar results.

This example demonstrates that the LRP is the predominant 39 kDa protein binding species on the $MH_1C_1$ cell surface.

Example 8 demonstrates that both the 39 kDa protein and t-PA specifically co-bind to a single LRP molecule.

EXAMPLE 8 t-PA and the 39 kDa Protein can be Cross-linked to the Same LRP Receptor Complex 0.5 nM $^{125}$I-39 kDa protein and 20 nM unlabelled t-PA were co-bound to $MH_1C_1$ cells both in the presence and absence of an excess of unlabelled 39 kDa protein. Following several washes to remove non-specifically associated ligand, cell monolayers were either incubated in 1 mM DTSSP or in PBSc alone. Once cross-linked, cell monolayers were washed, lysed and immunoprecipitated as described above.

FIG. 8 shows the results from a typical experiment. When the $^{125}$I-39 kDa protein and unlabelled t-PA were co-bound to the $MH_1C_1$ cell surface and incubated in the absence of cross-linker (FIGSS. 8C and D), the radiolabelled 39 kDa protein was immunoprecipitated from cell lysates with only the α-39 kDa antibody (arrowhead). Neither the α-LRP antibody nor the α-t-PA antibody showed any affinity for the radiolabelled 39 kDa ligand. Samples electrophoresed under both reducing and non-reducing conditions gave similar results. As in Example 3, interaction of the 39 kDa protein with the $MH_1C_1$ cell surface was shown to be specific by abrogation with an excess of unlabelled 39 kDa protein. When $MH_1C_1$ cells were pre-bound with $^{125}$I-39 kDa protein and unlabelled t-PA, and incubated in the presence of cross-linker (FIGS. 8A and B), a high molecular weight complex of ligand-associated radioactivity resulted, which was immunoprecipitable with α-39 kDa, α-t-PA, and α-LRP antibodies. Each of these interactions was specific, as each was abolished in samples incubated in the presence of an excess of unlabelled 39 kDa protein. This protein complex of $^{125}$I-39 kDa, t-PA, and LRP was of very high apparent molecular weight as before, remaining largely in the stacking gel during electrophoresis (arrows). When these same samples were electrophoresed in the presence of 2-mercaptoethanol to cleave the cross-linker, each resulted in a single radiolabelled band corresponding to the exogenously added $^{125}$I-39 kDa protein (arrowhead).

In order to determine if cross-linking of the 39 kDa protein to the $MH_1C_1$ cell surface generates an epitope for recognition by the α-t-PA antibody, similar experiments were performed with $^{125}$I-39 kDa protein bound and cross-linked to the $MH_1C_1$ cell surface, but in the absence of exogenously added, unlabelled t-PA (FIGS. 8E and F). In this case, the high molecular weight complex of ligand-associated radioactivity was immunoprecipitable only with α-LRP and α-39 kDa antibodies, and not with the α-t-PA antibody.

This experiment shows that the simple cross-linking of radiolabelled 39 kDa protein to the $MH_1C_1$ cell surface does not change its specificity for either the α-t-PA or α-39 kDa antibodies. A number of additional co-binding and cross-linking experiments, performed using $^{125}$I-t-PA and unlabelled 39 kDa protein, gave similar results (data not shown). This data taken together with the data presented above leads to the conclusion that the 39 kDa protein and t-PA can bind simultaneously to LRP on the $MH_1C_1$ cell surface.

It was found from the following examples that endocytosis of the 39 kDa protein is receptor-mediated like t-PA and that the 39 kDa protein modulates the receptor-mediated endocytosis of t-PA.

EXAMPLE 9

Rapid Uptake and Degradation of $^{125}$I-39 kDa by $MH_1C_1$ Cells

It is known that $MH_1C_1$ cells rapidly endocytose and degrade t-PA (Bu, G. et al., (1992) J. Biol. Chem. 267, 15595–15602). The following single cycle uptake and degradation experiments demonstrate that $MH_1C_1$ cells similarly endocytose the 39 kDa protein.

Endocytosis experiments were performed according to Ciechanover et al., (1983) J. Biol. Chem. 258, 9681–9689 and Owensby et al., (1988) J. Biol. Chem. 263, 10587–10594. 6 well dishes containing $10^6$ cells/well were preincubated at 4° C. with 14 nM $^{125}$I-39 kDa protein to allow binding. Following three washes with PBSc (4° C.) to remove non-specifically associated ligand, each dish was incubated at 37° C., and a pre-warmed solution of 200 nM unlabelled 39 kDa protein was added to initiate internalization. At each time point, over a period of 60 minutes, one of the dishes was cooled directly on ice, and the overlying media was removed. Precipitation of the overlying media was carried out by the addition of bovine serum albumin to 10 mg/ml and trichloroacetic acid (TCA) to 20%. Both the TCA soluble (i.e., extracellular degraded ligand) and TCA insoluble (i.e., extracellular dissociated ligand) fractions were counted by γ scintillation spectrometry.

In addition, cell monolayers were washed three times with PBSc and incubated 30 minutes at 4° C. with a solution of PBSc containing 0.25% Pronase (Calbiochem) to digest membraneassociated ligand. Cells were subsequently removed from each well and pelleted by centrifugation at 12,000 g. Both the cell pellets and the supernatants following Pronase treatment were counted by γ scintillation spectrometry to determine both cell associated (i.e., protease resistant) and membrane-associated (i.e., protease sensitive) reactivity.

FIG. 9 shows the results from a typical experiment. As expected, all ligand-associated radioactivity was initially located at the cell surface. Within 3 minutes of warm-up, however, 80% of this population became intracellular (protease resistant) or dissociated into the-media as TCA insoluble (undegraded ligand) counts. The intracellular levels of ligand reached a peak value of 50% of total at approximately 10 minutes. Concurrently, the TCA soluble radioactivity, representing internalized and subsequently degraded ligand, appeared in the overlying media initially at 10 minutes, with plateau levels reached at between 45 and 60 minutes. This kinetic pattern of uptake and degradation of a single cohort of pre-bound $^{125}$I-39 kDa ligand was identical to that observed for $^{125}$I-t-PA with these $MH_1C_1$ cells.

EXAMPLE 10

Inhibition of $^{125}$I-t-PA Uptake and Degradation by the 39 kDa Protein on HepG2 Cells The receptor-mediated endocytosis of the t-PA:PAI-1 complex by HepG2 cells has been previously demonstrated. (See, Owensby, D. A. et al., (1988) J. Biol. Chem. 263, 10587–10594; Morton, P. A. et al., (1989) J. Biol. Chem. 264, 7228–7235; Underhill, D. M. et al., (1992) Blood 80, 2746–2754). It was found from the following experiment that the endocytosis and degradation of the t-PA:PAI-1 complex by HepG2 cells were also via LRP and that the 39 kDa protein inhibits the endocytosis and degradation of $^{125}$I-t-PA.

Throughout this example, protein concentration was determined using a Bio-Rad protein assay with bovine serum albumin as a standard. Cell number was determined by counting cells with a hemocytometer.

Ligand Uptake and Degradation

HepG2 cell monolayers seeded in 6-well dishes were incubated at 37° C. with 3 nM $^{125}$I-t-PA in the absence or presence of various competitors at selected concentrations. After selected intervals, binding buffer overlying cell monolayers was collected, cell monolayers were chilled on ice and washed with prechilled binding buffer for three times to prevent further ligand uptake and degradation. Cellular degradation of radiolabelled ligand was determined by measuring the appearance of TCA-soluble radioactivity in the overlying buffer, whereas cell-associated radioactivity was determined by lysing the cell monolayers in the low-SDS lysis buffer and measuring the total radioactivity in the cell lysates. Cell-mediated degradation of $^{125}$I-t-PA was monitored in the absence or presence of an excess of one of the following competitor proteins: t-PA, 39 kDa protein, or BSA.

The results shown in FIG. 10A demonstrate that, in the absence of any competitor protein, the degradation of $^{125}$I-t-PA (initial concentration=3 nM) increased almost linearly for at least 4 hours. This observation suggests the existence of an intracellular receptor pool and recycling of the t-PA receptors. (See, Owensby, D. A. et al., (1988) J. Biol. Chem. 263, 10587–10594; Morton, P. A. et al., (1989) J. Biol. Chem. 264, 7228–7235). Excess unlabelled t-PA (1 μM) reduced the degradation of $^{125}$I-t-PA to about 10% which represents the nonspecific degradation of the ligand. When the 39 kDa protein was included in the incubation, specific degradation of $^{125}$I-t-PA was inhibited by about 75%. This is consistent with the majority of the specific degradation occurring via LRP. This degree of inhibition of $^{125}$I-t-PA degradation by the 39 kDa protein is similar to the degree of inhibition of $^{125}$I-t-PA binding by the 39 kDa protein (see FIG. 5). The control protein BSA had no effect on $^{125}$I-t-PA degradation.

To confirm that the inhibition of $^{125}$I-t-PA degradation by the 39 kDa protein occurs at the step of ligand uptake rather than intracellular degradation, the cell-associated radioactivity was quantitated during the first hour of endocytosis. As shown in FIG. 10B, about 70% of the specific $^{125}$I-t-PA uptake was inhibited by the 39 kDa protein, whereas the control protein BSA showed no inhibitory effect on this process.

These results clearly demonstrate that LRP serves as the major PAI-1-dependent endocytosis receptor for t-PA on HepG2 cells, and that the 39 kDa LRP receptor-associated protein modulates this interaction.

$MH_1C_1$ cells rapidly catabolize the 39 kDa protein as shown in Example 11.

EXAMPLE 11

Rate of 39 kDa Protein Uptake by $MH_1C_1$ Cells

The following experiment used the procedure described in Schwartz, A. L. et al., (1982) J. Biol. Chem. 257, 4230–4237.

Rate of 39 kDa Protein Uptake

Dishes containing monolayers of $10^6$ $MH_1C_1$ cells/well were cooled on ice and washed three times with cold PBSc. Ligand uptake was initiated by the addition of prewarmed (37° C.) binding buffer containing 28 nM $^{125}$I-39 kDa proteins either in the presence or absence of an excess of unlabelled 39 kDa protein. Each dish was incubated at 37° C. for a period of between 0 and 120 minutes. At each time point, one of the dishes was cooled directly on ice, and the overlying media was removed. Cell monolayers were washed three times with PBSc and lysed in low SDS lysis buffer for the determination of cell associated radioactivity. Each sample of overlying media was precipitated with TCA as described in Example 9, and the TCA soluble fraction was counted by γ scintillation spectrometry.

FIG. 11 shows the results from a typical experiment. The amount of cell-associated ligand increased rapidly, reaching a plateau at approximately 40 minutes after the transition in temperature. The amount of extracellular degraded ligand exhibited a lag of approximately 20 minutes, after which there began a linear increase which lasted the duration of the experiment. The sum of both cell-associated and extracellular degraded ligand also increased linearly with a slope identical to that of extracellular degraded ligand alone. The slopes of each of these parameters was a measure of the rate of ligand uptake and degradation at 37° C. and was determined to be 52 fmol/$10^6$ cells/minute. This experiment demonstrates a pattern of rapid catabolism of the 39 kDa protein by $MH_1C_1$ cells.

The following examples demonstrate that the 39 kDa protein inhibits t-PA binding to hepatic receptors.

EXAMPLE 12

Rat 39 kDa Protein Can Efficiently Inhibit t-PA Binding to Cells

Using the procedure described in Example 3, the $^{125}$I-t-PA binding analyses described below showed the kinetics of inhibition of t-PA binding to $MH_1C_1$ cells by the native rat 39 kDa protein. FIG. 12 shows the results of $^{125}$I-t-PA binding analyses performed in the presence of varying concentrations of either unlabelled t-PA or recombinant rat 39 kDa protein as competitors. Unlabelled t-PA inhibits binding of $^{125}$I-t-PA with an apparent $K_i$ value of 8 nM (FIG. 12B). The 39 kDa protein, on the other hand, competed at a much lower concentration, with an apparent $K_i$ value of 0.5 nM (FIG. 12A). This experiment demonstrates that the 39 kDa protein is a strong competitor for $^{125}$I-t-PA binding to LRP on the $MH_1C_1$ cell surface.

EXAMPLE 13

Inhibition of $^{125}$I-t-PA:PAI-1 Complex Binding to HepG2 Cells by 39 kDa Protein and Anti-LRP Antibody In the following ligand binding competition experiments, it was found that PAI-1-dependent $^{125}$I-t-PA binding was also mediated via LRP. Specific binding of 3 nM $^{125}$I-t-PA was performed in the absence or presence of each of three competitor proteins: t-PA, 39 kDa protein, or bovine serum albumin (BSA). Each competitor protein was included at increasing concentrations up to more than 100-fold molar excess of the radiolabelled ligand. Throughout this example, protein concentration was determined using a Bio-Rad protein assay with bovine serum albumin as a standard. Cell number was determined by counting cells with a hemocytometer.

Ligand Binding Competition Assays

Binding of the $^{125}$I-labelled ligand was performed as described above in Example 4 in the absence or presence of various competitors at selected concentrations. In those experiments in which both t-PA and 39 kDa protein were involved, the t-PA binding buffer was used. Nonspecific binding was determined in the presence of 1 μM unlabelled ligand.

Figure 5A:
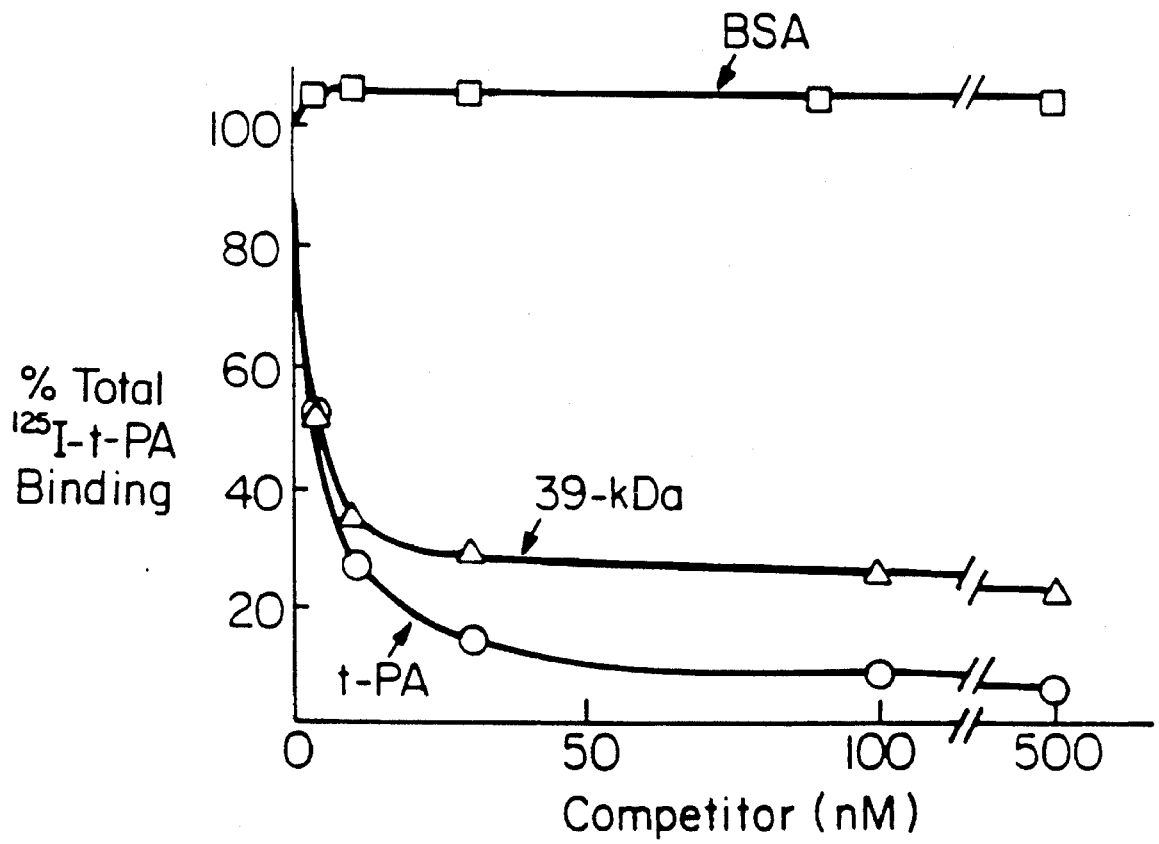
FIG. 5A is a graph of the inhibition of 3 nM $^{125}$I-t-PA binding to HepG2 cells by the 39 kDa protein in the absence or presence of increasing concentrations of competitor proteins. Each symbol represents the average of duplicate determinations and the standard deviations are less than 5%.

As shown in FIG. 5A, unlabelled t-PA competed with $^{125}$I-t-PA for binding with an apparent $K_i$ of about 3 nM. The 39 kDa protein also inhibited specific $^{125}$I-t-PA binding to a maximum of about 80% (FIG. 5A). The control protein BSA had no effect on specific $^{125}$I-t-PA binding indicating that inhibition by the 39 kDa protein was not due to a generalized effect but was specific. These results with the 39 kDa protein suggest that the majority of the PAI-1-dependent $^{125}$I-t-PA binding on the HepG2 cells is via LRP. The observation that the 39 kDa protein inhibits only 80% of specific $^{125}$I-t-PA binding may indicate the presence of a minor population of t-PA binding sites that are not accessible to or inhibited by the 39 kDa protein.

Figure 5B:
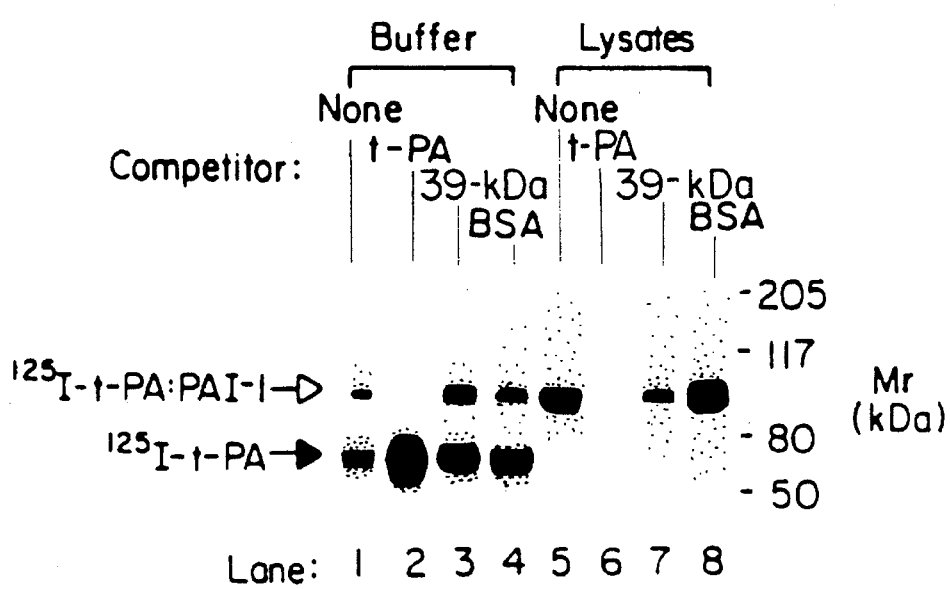
FIG. 5B is a SDS polyacrylamide gel (7.5%) of post-binding buffers overlying cell monolayers and corresponding cell lysates where the gel was analyzed under nonreducing conditions using a sample buffer containing low concentration of SDS (0.2%). Samples were selected from either no competitor protein (lanes 1 and 5), or with 500 nM t-PA (lanes 2 and 6), 500 nM 39 kDa protein (lanes 3 and 7), or 500 nM BSA (lanes 4 and 8).

To test whether inhibition of $^{125}$I-t-PA binding by the 39 kDa protein was due to interference with formation of the complex between $^{125}$I-t-PA and endogenous PAI-1, post-binding buffer overlying cell monolayers from the binding assays of FIG. 5A (without any competitor protein or from each of those with 500 nM competitor protein) was analyzed by SDS-PAGE (FIG. 5B). The $^{125}$I-t-PA:PAI-1 complex can be seen in the absence of excess unlabelled t-PA (lane 1), but not in the presence of excess unlabelled t-PA (lane 2). Inclusion of excess unlabelled 39 kDa protein did not interfere with the formation of the $^{125}$I-t-PA:PAI-1 complex (lane 3). The $^{125}$I-t-PA:PAI-1 complex observed in the presence of the 39 kDa protein is greater than that seen with $^{125}$I-t-PA alone and presumably reflects the inhibition of complex binding to HepG2 cells by the 39 kDa protein. Cell lysates corresponding to the overlying buffer shown in lane 1–4 were also analyzed via the same SDS polyacylamide gel (FIG. 5B). Binding of the $^{125}$I-t-PA:PAI-1 complex to HepG2 cells is demonstrated in the cell lysates without competitor protein (lane 5). When excess unlabelled t-PA was included, however, specific binding of the $^{125}$I-t-PA:PAI-1 complex was absent (lane 6). When the cell lysate with 500 nM 39 kDa protein was compared to that with $^{125}$I-t-PA alone, specific $^{125}$I-t-PA:PAI-1 complex binding was reduced by about 80% (lane 7). The control protein BSA neither interfered with the complex formation (lane 4) nor inhibited specific $^{125}$I-t-PA:PAI-1 complex binding (lane 8). These results thus demonstrate that the inhibition of $^{125}$I-t-PA binding to HepG2 cells by the 39 kDa protein occurs at the level of $^{125}$I-t-PA:PAI-1 binding to LRP without interference with the initial complex formation.

Modulation of ligand binding to LRP by the 39 kDa protein is not due to competition at a single site with various ligands since previous experiments have shown that LRP ligands (e.g., $\alpha_2$M*, t-PA) compete only slightly with the 39 kDa protein for binding to LRP. (See, Bu, G. et al., (1992) Proc. Natl. Acad. Sci. USA 89, 7427–7431). To test whether $^{125}$I-39 kDa protein binding is affected by t-PA on HepG2 cells, ligand binding competition experiments were performed. Competitor proteins (t-PA, 39 kDa protein, or BSA) at various concentrations were included in $^{125}$I-39 kDa protein binding. As shown in FIG. 13, specific binding of $^{125}$I-39 kDa protein was reduced only slightly (about 20%) by excess unlabelled t-PA, whereas the binding was completely inhibited by excess unlabelled 39 kDa protein. These results suggest that the 39 kDa protein inhibits t-PA:PAI-1 complex binding indirectly perhaps via inducing a conformational change in LRP unfavorable to t-PA:PAI-1 complex binding. Alternatively, t-PA:PAI-1 complex binding sites on HepG2 cells may account for only a small portion of the 39 kDa protein binding sites with most of the binding sites distributed over other parts of the LRP molecule not shared with t-PA.

To test directly whether the majority of PAI-1-dependent $^{125}$I-t-PA binding sites is on LRP, ligand binding competition experiments were performed in the presence of anti-LRP antibody. This rabbit polyclonal antibody was generated using purified human placental LRP as antigen. The total IgG fraction was purified and used for competition of $^{125}$I-t-PA binding (3 nM). Non-immune rabbit IgG was used as a control. As shown in FIG. 14, specific binding of the $^{125}$I-t-PA:PAI-1 complex was reduced by up to 75%, while non-immune IgG had little or no effect. The percentage of reduction on specific $^{125}$I-t-PA binding by anti-LRP antibody (i.e. approximately 75%) is similar to that seen with the 39 kDa protein (see FIG. 5), further supporting the observation that the predominant binding (~70–80%) of the $^{125}$I-t-PA:PAI-1 complex on HepG2 cells is mediated by LRP.

In the following example, it was found that the 39 kDa protein effectively inhibited hepatic clearance of t-PA in both in vitro and in vivo experiments.

EXAMPLE 14

Effect of 39 kDa Protein on Hepatic Clearance of t-PA 39 kDa Protein Preparation The 39 kDa protein was isolated from 5 liters of E.coli containing the recombinant plasmid according to Example 1 and yielded the GST-39 kDa protein. Following thrombin cleavage and removal of the GST, the 39 kDa protein was approximately 95% pure as determined by SDS-PAGE and Coomassie/silver staining. The few percent of non-39 kDa protein contained within these preparations were unabsorbed fragments of GST. In order to provide a homogeneously pure preparation of 39 kDa protein, this partially purified mixture was applied to a heparin agarose column (Sigma Chemical Co.). Following extensive washing with 100 mM NaCl to remove contaminating proteins, the 39 kDa protein was eluted at 0.4M NaCl. This preparation resulted in the greater than 99% homogenous preparation of 39 kDa protein as determined by SDS-PAGE and Coomassie/silver staining and shown in FIG. 15.

General Procedures

The following procedures were used throughout this example.

1. Cell Culture

Rat hepatoma $MH_1C_1$ cells were cultured in accordance with the procedure of Example 3.

2. Protein Iodination t-PA, 39 kDa protein, GST, $\alpha$1-acid glycoprotein (orosomucoid, OR), and the asialo form of $\alpha$1-acid glycoprotein (ASOR) were iodinated with $^{125}$I as described in Example 4. The specific activity of the resultant labelled proteins was 5–10 µCi/µg of protein.

3. Protein Concentration Determination

Protein concentration was determined using the Biorad protein assay with bovine serum albumin as a standard.

Ligand Binding Assays

Bioactivity was determined on this preparation of 39 kDa protein by its ability to inhibit $^{125}$I-t-PA to $MH_1C_1$ cells as described in Example 9. Wells containing approximately $10^5$ $MH_1C_1$ cells were washed and preincubated at 4° C. with binding buffer containing the indicated concentrations of unlabelled t-PA or unlabelled 39 kDa protein in addition to 3 nM $^{125}$I-t-PA. Following incubation for 1.5 hours at 4° C., the medium was removed, the cells washed and the specific $^{125}$I-t-PA binding was determined based on the radioactivity measured in accordance with the procedure of Example 4. As seen in FIG. 15, this preparation of 39 kDa protein is biologically active against the t-PA receptor with 50% inhibition seen at <1 nM.

In vivo Clearance Determinations

In vivo clearance determinations were performed in the following manner on 200 gm female Sprague-Dawley rats obtained from Charles River Breeders and fed standard lab chow ad lib. Following anesthesia with 12 mg Nembutal, the tail vein was catheterized and a 250 µl solution containing the test protein in normal saline was infused over 30 seconds. Repetitive samples were obtained from the distal tail artery into cooled microtubes containing 2 μl heparin (1:1000). Routinely samples were collected at 30 seconds, 1, 2, 4, 6, 8 and 10 minutes. After the 10 minute peripheral sample was collected, a central blood sample was collected by an open cardiac puncture and the visceral organs (liver, kidney, spleen) were rapidly removed to ice. Aliquots of the liver and entire kidney and spleen were counted for radioactivity determination. Heparinized blood samples were centrifuged to separate plasma from blood cells and an aliquot of plasma, generally 25 μl, was spotted onto Whatman 3M paper, dried, precipitated in 10% trichloracetic acid and radioactivity determined in a Packard Gamma Spectrophotometer.

1. Clearance of t-PA

To demonstrate that t-PA is rapidly cleared from the blood plasma following intravenous administrations adult 200 g rats were anesthetized and administered 30 pmol $^{125}$I-t-PA via venous injection as described above. Arterial blood samples were collected at the indicated times, separated and plasma radioactivity determined.

As seen in FIG. 16A, following intravenous administration to each of the eight rats of 30 pmol of $^{125}$I-t-PA, the plasma $^{125}$I-t-PA was rapidly cleared with a $t_{1/2}$ of approximately one minute. Less than 10% of the $^{125}$I-t-PA remained in blood plasma at 10 minutes. Analysis of the liver at 10 minutes following the administration revealed approximately 90% of the initial plasma radioactivity was found in liver.

2. Effect of Excess t-PA on t-PA Clearance

Intravenous administration to three rats of 400-fold molar excess unlabelled t-PA (12 nmol) one minute prior to administration of the identical dose of 30 pmol $^{125}$I-t-PA resulted in a marked reduction in the plasma clearance of $^{25}$I-t-PA as seen in FIG. 16A. The plasma half-life was approximately 9–10 minutes and approximately 40% of the $^{125}$I-t-PA remained in the blood at 10 minutes. Analysis of the liver at 10 minutes revealed approximately 70% of the initial plasma radioactivity was found in liver.

3. Effect of 39 kDa Protein on t-PA Clearance

Intravenous administration to four rats of 250 nmol of unlabelled 39 kDa protein (8,000-fold molar excess) one minute prior to administration of the identical 30 pmol $^{125}$I-t-PA also resulted in a marked reduction in the plasma clearance of $^{125}$I-t-PA as seen in FIG. 16A. Plasma half-life was approximately 6 minutes. Approximately 30% of the $^{125}$I-t-PA remained in the blood at 10 minutes. Analysis of the liver at 10 minutes revealed approximately 80% of the initial plasma radioactivity was found in liver.

4. Clearance of 39 kDa Protein

A series of controlled clearance experiments were performed to determine the in vivo fate of the administered 39 kDa protein. Adult 200 g rats were anesthetized and administered 30 pmol $^{125}$I-39 kDa protein via venous injection. Arterial blood samples were collected at the indicated times, separated, and plasma radioactivity determined as described above. As seen in FIG. 17, following intravenous administration to the rat of 30 pmol of $^{125}$I-39 kDa protein, the plasma $^{125}$I-39 kDa protein was rapidly cleared with a $t_{1/2}$ of approximately one minute.

The following table, Table 2, shows that the analysis of the liver, kidney and spleen at 10 minutes revealed approximately 70% of the initial radioactivity in liver, 7% in kidney and less than 2% in spleen. Following plasma clearance of $^{125}$I-39 kDa protein in the rat in vivo as described in FIG. 17, the liver, kidney and spleen were harvested at 10 minutes and the radioactivity determined. Each figure is the mean±S.E.M.

TABLE 2

| ORGAN DISTRIBUTION OF $^{125}$I-39kDa PROTEIN | | | | |
|---|---|---|---|---|
| Preadministration (dose) | $^{125}$I-39kDa Protein (dose) | Liver | Kidney | Spleen |
| | | (% initial radioactivity) | | |
| a. none | 30 pmol | 69 ± 5 | 7 ± 1 | 2 ± 0.2 |
| b. 12.5 nmol | 30 pmol | 72 ± 3 | 12 ± 1 | 2 ± 0.2 |
| c. 50 nmol | 30 pmol | 25 ± 6 | 13 ± 2 | 2 ± 0.6 |
| d. 125 nmol | 30 pmol | 23 ± 5 | 31 ± 10 | 2 ± 0.3 |

The capacity for hepatic clearance of 39 kDa protein is large, but can be saturated as seen in FIG. 17 and Table 2. Intravenous administration of increasing doses of unlabelled kDa protein results in a decrease of the fraction of the initial dose found in the liver at 10 minutes. Concomitantly there is an increasing fraction of the initial dose found in the kidney, which indicates that maximal hepatic capacity of 39 kDa protein clearance can be readily achieved in vivo. Therefore multiple dosing schedules and/or continuous infusion of 39 kDa protein should markedly reduce hepatic t-PA clearance in vivo.

5. Effect of Excess 39 kDa Protein on 39 kDa Protein Clearance

Intravenous administration of 12.5 nmol of unlabelled 39 kDa protein one minute prior to administration of the identical 30 pmol of $^{125}$I-39 kDa protein resulted in a prolongation of the plasma half-life to approximately three minutes. Analysis of liver, kidney and spleen at 10 minutes revealed approximately 70% in liver, 12% in kidney, and less than 2% in spleen.

Intravenous administration of 50 nmol of unlabelled 39 kDa protein one minute prior to the identical 30 pmol of $^{125}$I- 39 kDa protein resulted in a further marked reduction in the plasma clearance of the $^{125}$I-39 kDa protein as seen in FIG. 17 with a half-life of approximately six minutes. Analysis of the liver, kidney and spleen at 10 minutes revealed approximately 30% liver, 15% in kidney and less than 2% in spleen.

Intravenous administration of 125 nmol of unlabelled 39 kDa protein one minute prior to administration of the identical 30 pmol of $^{125}$I-39 kDa protein resulted in a further marked reduction in the plasma clearance of the $^{125}$I-39 kDa protein with a plasma half-life of approximately 9 minutes. Analysis of the liver, kidney and spleen revealed approximately 22% in liver, 33% in kidney and less than 2% in spleen.

6. Clearance of Other Proteins

Not all proteins administered to the rat intravenously are rapidly cleared by liver. Adult 200 g rats were anesthetized and administered via venous injection (a) 5 pmol $^{125}$I-α1-acid glycoprotein (OR), and (b) 5 pmol $^{125}$I-asialo-α1-acid glycoprotein (ASOR). Arterial blood samples were collected at the indicated times, separated, and plasma radioactivity determined as described above. As seen in FIG. 16B, for example, α1-acid glycoprotein was cleared with a half-time of greater than 90 minutes, whereas its asialo-derivative was rapidly cleared with half-time of approximately 0.5 minute (see Schwartz et al., (1984) CRC Crit. Rev. Biochem. 16, 207–233).

EXAMPLE 15

Effect of 39 kDa Protein Fragments on Hepatic Clearance of t-PA

The following experiment demonstrates that the entire 39 kDa protein molecule is not required for inhibition of t-PA binding to the hepatic t-PA receptor. The 39 kDa protein was chemically cleaved and the individual fragments isolated. These were then tested for inhibition of $^{125}$I-t-PA binding to receptors on rat hepatocyte cells. Throughout this example, protein concentration was determined using a Bio-Rad protein assay with bovine serum albumin as a standard.

Purified 39 kDa protein was prepared in accordance with the procedure of Example 14. In order to generate isolated fragments of the 39 kDa protein, acid hydrolysis was performed under strict conditions. The 39 kDa protein in 0.4M NaCl was incubated for 80 hours at room temperature in 70% formic acid. These acid proteolytic conditions provided for the complete cleavage of the intact 39 kDa protein at the Asp-Pro bond at amino acid residues 114–115 and the generation of two large fragments (~20 kDa N-terminal fragment and ~28 kDa C-terminal fragment) o Following separation on SDS-PAGE, the intact 39 kDa protein, the 20 kDa N-terminal fragment, and 28 kDa C-terminal fragment were electrophoretically transferred to PVDF paper in accordance with the procedure described in Matsudaira, F., *A Practical Guide to Protein and Peptide purification for Microsequences* (1989 Academic Press, New York). The appropriate polypeptide bands were visualized by staining representative gel lanes, cut out of the PVDF paper, and eluted by incubation for 1 hour at room temperature in 1% Triton X-100 in 50 mm Tris, pH 9.

Reanalysis by SDS-PAGE demonstrates single individual bands of the appropriate molecular weights for the intact 39 kDa protein, the 20 kDa N-terminal fragment, and the 28 kDa C-terminal fragments. Sequencing of these individual protein species at the Washington University Microchemical Core Facility confirmed cleavage of the intact 39 kDa protein at the $ASp_{114}$-$Pro_{115}$ bond.

Thereafter the biological activity of the intact 39 kDa protein, the 20 kDa N-terminal fragment, and the 28 kDa C-terminal fragment were tested by quantitating the inhibition of $^{125}$I-t-PA binding to rat liver $MH_1C_1$ cells. Cells were washed and preincubated at 4° C. in binding buffer containing 0–16 nM of the intact 39 kDa protein (●), the 20 kDa N-terminal fragment (■), the 28 kDa C-terminal fragment (▲), or PVDF-elution buffer alone (o) as a control. 4 nM $^{125}$I-t-PA was added and the incubation continued for 2 hours at 4° C. Following removal and washing of the unbound $^{125}$I-t-PA, the amount of radioactivity bound to the $MH_1C_1$ cells was determined as described in Example 14.

As shown in FIG. 18, the intact 39 kDa protein inhibited $^{125}$I-t-PA binding with 50% inhibition at approximately 1 nM and 90% inhibition at approximately 8–10 nM, consistent with previous observations (Bu et al., (1992) Proc. Natl. Acad. Sci. USA 89, 7427–7431; Examples 10, 120 13, and 14 above). The 20 kDa N-terminal fragment was essentially without effect i.e., approximately 10% inhibition at 16 nM; buffer alone exhibited 20–30% inhibition under these identical conditions). In marked contrast the 28 kDa C-terminal fragment was an extremely active inhibitor of $^{125}$I-t-PA binding with approximately 50% inhibition at 4 nM and 90% inhibition at 16 nM as shown in FIG. 18.

The nearly equipotent activity of the 28 kDa C-terminal fragment compared to intact 39 kDa protein strongly suggests that a small fragment of the 39 kDa protein, which could include a fragment that overlaps the dividing point between the 20 kDa N-terminal fragment and 28 kDa C-terminal fragment, or a chemically or genetically related/ modified form of the molecule, will be recognized by the t-PA hepatic receptor and may serve as a powerful reagent in inhibiting t-PA clearance in vivo.

SEQUENCE LISTING ( 1 ) GENERAL INFORMATION:

( i i i ) NUMBER OF SEQUENCES: 5

( 2 ) INFORMATION FOR SEQ ID NO: 1:

( i ) SEQUENCE CHARACTERISTICS:
        ( A ) LENGTH: 323 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 1:

```
Tyr  Ser  Arg  Glu  Lys  Asn  Gln  Pro  Lys  Pro  Ser  Pro  Lys  Arg  Glu  Ser
 1                    5                      10                      15

Gly  Glu  Glu  Phe  Arg  Met  Glu  Lys  Leu  Asn  Gln  Leu  Trp  Glu  Lys  Ala
                     20                      25                      30

Gln  Arg  Leu  His  Leu  Pro  Pro  Val  Arg  Leu  Ala  Glu  Leu  His  Ala  Asp
                35                      40                      45

Leu  Lys  Ile  Gln  Glu  Arg  Asp  Glu  Leu  Ala  Trp  Lys  Lys  Leu  Lys  Leu
```

|     |     |     |     | 50  |     |     |     |     | 55  |     |     |     |     | 60  |     |
| --- | --- | --- | --- | --- | --- | --- | --- | --- | --- | --- | --- | --- | --- | --- | --- |
| Asp | Gly | Leu | Asp | Glu | Asp | Gly | Glu | Lys | Glu | Ala | Arg | Leu | Ile | Arg | Asn |
| 65  |     |     |     |     | 70  |     |     |     |     | 75  |     |     |     |     | 80  |
| Leu | Asn | Val | Ile | Leu | Ala | Lys | Tyr | Gly | Leu | Asp | Gly | Lys | Lys | Asp | Ala |
|     |     |     |     | 85  |     |     |     |     | 90  |     |     |     |     | 95  |     |
| Arg | Gln | Val | Thr | Ser | Asn | Ser | Leu | Ser | Gly | Thr | Gln | Glu | Asp | Gly | Leu |
|     |     |     | 100 |     |     |     |     | 105 |     |     |     |     | 110 |     |     |
| Asp | Asp | Pro | Arg | Leu | Glu | Lys | Leu | Trp | His | Lys | Ala | Lys | Thr | Ser | Gly |
|     |     | 115 |     |     |     |     | 120 |     |     |     |     | 125 |     |     |     |
| Lys | Phe | Ser | Gly | Glu | Glu | Leu | Asp | Lys | Leu | Trp | Arg | Glu | Phe | Leu | His |
|     |     | 130 |     |     |     |     | 135 |     |     |     |     | 140 |     |     |     |
| His | Lys | Glu | Lys | Val | His | Glu | Tyr | Asn | Val | Leu | Leu | Glu | Thr | Leu | Ser |
| 145 |     |     |     |     | 150 |     |     |     |     | 155 |     |     |     |     | 160 |
| Arg | Thr | Glu | Glu | Ile | His | Glu | Asn | Val | Ile | Ser | Pro | Ser | Asp | Leu | Ser |
|     |     |     |     | 165 |     |     |     |     | 170 |     |     |     |     | 175 |     |
| Asp | Ile | Lys | Gly | Ser | Val | Leu | His | Ser | Arg | His | Thr | Glu | Leu | Lys | Glu |
|     |     |     | 180 |     |     |     |     | 185 |     |     |     |     | 190 |     |     |
| Lys | Leu | Arg | Ser | Ile | Asn | Gln | Gly | Leu | Asp | Arg | Leu | Arg | Arg | Val | Ser |
|     |     | 195 |     |     |     |     | 200 |     |     |     |     | 205 |     |     |     |
| His | Gln | Gly | Tyr | Ser | Thr | Glu | Ala | Glu | Phe | Glu | Glu | Pro | Arg | Val | Ile |
|     |     | 210 |     |     |     |     | 215 |     |     |     |     | 220 |     |     |     |
| Asp | Leu | Trp | Asp | Leu | Ala | Gln | Ser | Ala | Asn | Leu | Thr | Asp | Lys | Glu | Leu |
| 225 |     |     |     |     | 230 |     |     |     |     | 235 |     |     |     |     | 240 |
| Glu | Ala | Phe | Arg | Glu | Glu | Leu | Lys | His | Phe | Glu | Ala | Lys | Ile | Glu | Lys |
|     |     |     |     | 245 |     |     |     |     | 250 |     |     |     |     | 255 |     |
| His | Asn | His | Tyr | Gln | Lys | Gln | Leu | Glu | Ile | Ala | His | Glu | Lys | Leu | Arg |
|     |     |     | 260 |     |     |     |     | 265 |     |     |     |     | 270 |     |     |
| His | Ala | Glu | Ser | Val | Gly | Asp | Gly | Glu | Arg | Val | Ser | Arg | Ser | Arg | Glu |
|     |     |     | 275 |     |     |     |     | 280 |     |     |     |     | 285 |     |     |
| Lys | His | Ala | Leu | Leu | Glu | Gly | Arg | Thr | Lys | Glu | Leu | Gly | Tyr | Thr | Val |
|     |     | 290 |     |     |     |     | 295 |     |     |     |     | 300 |     |     |     |
| Lys | Lys | His | Leu | Gln | Asp | Leu | Ser | Gly | Arg | Ile | Ser | Arg | Ala | Arg | His |
| 305 |     |     |     |     | 310 |     |     |     |     | 315 |     |     |     |     | 320 |
| Asn | Glu | Leu |     |     |     |     |     |     |     |     |     |     |     |     |     |

( 2 ) INFORMATION FOR SEQ ID NO: 2:

( i ) SEQUENCE CHARACTERISTICS:
        ( A ) LENGTH: 209 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 2:

| Pro | Arg | Leu | Glu | Lys | Leu | Trp | His | Lys | Ala | Lys | Thr | Ser | Gly | Lys | Phe |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Ser | Gly | Glu | Glu | Leu | Asp | Lys | Leu | Trp | Arg | Glu | Phe | Leu | His | His | Lys |
|     |     |     | 20  |     |     |     |     | 25  |     |     |     |     | 30  |     |     |
| Glu | Lys | Val | His | Glu | Tyr | Asn | Val | Leu | Leu | Glu | Thr | Leu | Ser | Arg | Thr |
|     |     |     | 35  |     |     |     |     | 40  |     |     |     |     | 45  |     |     |
| Glu | Glu | Ile | His | Glu | Asn | Val | Ile | Ser | Pro | Ser | Asp | Leu | Ser | Asp | Ile |
|     |     |     | 50  |     |     |     |     | 55  |     |     |     |     | 60  |     |     |
| Lys | Gly | Ser | Val | Leu | His | Ser | Arg | His | Thr | Glu | Leu | Lys | Glu | Lys | Leu |
| 65  |     |     |     |     | 70  |     |     |     |     | 75  |     |     |     |     | 80  |

| Arg | Ser | Ile | Asn | Gln | Gly | Leu | Asp | Arg | Leu | Arg | Arg | Val | Ser | His | Gln |
|-----|-----|-----|-----|-----|-----|-----|-----|-----|-----|-----|-----|-----|-----|-----|-----|
|     |     |     | 85  |     |     |     |     |     | 90  |     |     |     |     | 95  |     |

| Gly | Tyr | Ser | Thr | Glu | Ala | Glu | Phe | Glu | Glu | Pro | Arg | Val | Ile | Asp | Leu |
|-----|-----|-----|-----|-----|-----|-----|-----|-----|-----|-----|-----|-----|-----|-----|-----|
|     |     |     | 100 |     |     |     |     |     | 105 |     |     |     | 110 |     |     |

| Trp | Asp | Leu | Ala | Gln | Ser | Ala | Asn | Leu | Thr | Asp | Lys | Glu | Leu | Glu | Ala |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Phe | Arg | Glu | Glu | Leu | Lys | His | Phe | Glu | Ala | Lys | Ile | Glu | Lys | His | Asn |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| His | Tyr | Gln | Lys | Gln | Leu | Glu | Ile | Ala | His | Glu | Lys | Leu | Arg | His | Ala |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Glu | Ser | Val | Gly | Asp | Gly | Glu | Arg | Val | Ser | Arg | Ser | Arg | Glu | Lys | His |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Ala | Leu | Leu | Glu | Gly | Arg | Thr | Lys | Glu | Leu | Gly | Tyr | Thr | Val | Lys | Lys |
|-----|-----|-----|-----|-----|-----|-----|-----|-----|-----|-----|-----|-----|-----|-----|-----|
|     |     |     | 180 |     |     |     |     | 185 |     |     |     | 190 |     |     |     |

| His | Leu | Gln | Asp | Leu | Ser | Gly | Arg | Ile | Ser | Arg | Ala | Arg | His | Asn | Glu |
|-----|-----|-----|-----|-----|-----|-----|-----|-----|-----|-----|-----|-----|-----|-----|-----|
|     |     | 195 |     |     |     |     | 200 |     |     |     |     | 205 |     |     |     |

Leu ( 2 ) INFORMATION FOR SEQ ID NO: 3:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO: 3:

CCGCGTGGAT CCCCCAGGCT GGAAAAGCTG TGG    33

( 2 ) INFORMATION FOR SEQ ID NO: 4:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO: 4:

TCAATGAATT CTCAGAGTTC GTTGTGCCGA GCTCT    35

( 2 ) INFORMATION FOR SEQ ID NO: 5:

( i ) SEQUENCE CHARACTERISTICS:
        ( A ) LENGTH: 205 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 5:

| Pro | Arg | Leu | Glu | Lys | Leu | Trp | His | Lys | Ala | Lys | Thr | Ser | Gly | Ile | Ser |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Val | Arg | Leu | Thr | Ser | Cys | Ala | Arg | Val | Leu | His | Tyr | Lys | Glu | Lys | Ile |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| His | Glu | Tyr | Asn | Val | Leu | Leu | Asp | Thr | Leu | Ser | Arg | Ala | Glu | Glu | Gly |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Tyr | Glu | Asn | Leu | Leu | Ser | Pro | Ser | Asp | Met | Thr | His | Ile | Lys | Ser | Asp |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

-continued

```
Thr Leu Ala Ser Lys His Ser Glu Leu Lys Asp Arg Leu Arg Ser Ile
 65              70                  75                  80

Asn Gln Gly Leu Asp Arg Leu Arg Lys Val Ser His Gln Leu Arg Pro
             85                  90                  95

Ala Thr Glu Phe Glu Glu Pro Arg Val Ile Asp Leu Trp Asp Leu Ala
            100             105             110

Gln Ser Ala Asn Phe Thr Glu Lys Glu Leu Glu Ser Phe Arg Glu Glu
        115             120             125

Leu Lys His Phe Glu Ala Lys Ile Glu Lys His Asn His Tyr Gln Lys
    130             135             140

Gln Leu Glu Ile Ser His Gln Lys Leu Lys His Val Glu Ser Ile Gly
145             150             155             160

Asp Pro Glu His Ile Ser Arg Asn Lys Glu Lys Tyr Val Leu Leu Glu
                165             170             175

Glu Lys Thr Lys Glu Leu Gly Tyr Lys Val Lys Lys His Leu Gln Asp
            180             185             190

Leu Ser Ser Arg Val Ser Arg Ala Arg His Asn Glu Leu
        195             200
```

The above description is meant to be illustrative of the present invention, and not limiting thereof. All explanations of the inventors theory of the invention are for illustrative purposes only. It is the inventors' intention that the scope of their invention be defined solely by the following claims.

We claim:

1. A 28 kDa protein having an amino acid sequence as set forth in SEQ ID NO:2:

```
1              10                  20
PRLEKLWHKAKTSGKFSGEELDKLWR 30          40          50
EFLHHKEKVHEYNVLLETLSRTEEIHE 60          70          80
NVISPSDLSDIKGSVLHSRHTELKEKLR 90              100
SINQGLDRLRRVSHQGYSTEAEFEEPR 110         120         130
VIDLWDLAQSANLTDKELEAFREELKH 140         150         160
FEAKIEKHNHYQKQLEIAHEKLRHAES 170             180
VGDGERVSRSREKHALLEGRTKELGYT 190         200         209
VKKHLQDLSGRISRARHNEL .
```

2. In a pharmaceutical composition for a mammalian patient containing tissue-type plasminogen activator (t-PA), the improvement comprising said composition further including a t-PA hepatic clearance-inhibiting amount of a protein selected from the group consisting of a 39 kDa protein having the amino acid sequence set forth in SEQ ID NO: 1 and the 28 kDa protein of claim 1.

3. The pharmaceutical composition of claim 2, wherein the t-PA is present in a dosage amount of from about 0.15 to 1.5 mg/kg of body weight/dose.

4. The pharmaceutical composition of claim 2, wherein the 39 kDa protein is present in a dosage amount of from about 60 to 6,000 mg/kg of body weight/dose.

5. The pharmaceutical composition of claim 2, wherein the 28 kDa protein is present in a dosage amount of from about 38 to 3,800 mg/kg of body weight/dose.

6. A composition for treating thrombolytic diseases in a mammal comprising tissue-type plasminogen activator (t-PA) in an amount which is effective for treating said thrombolytic diseases, and a t-PA hepatic clearance-inhibiting protein selected from the group consisting of a 39 kDa protein having the amino acid sequence set forth in SEQ ID NO: 1 and the 28 kDa protein of claim 1 in an amount which is effective for inhibiting hepatic clearance of t-PA.

7. The composition of claim 6, wherein the t-PA is present in a dosage amount of from about 0.15 to 1.5 mg/kg of body weight/dose.

8. The composition of claim 6, wherein the 39 kDa protein thereof is present in a dosage amount of from about 60 to 6,000 mg/kg of body weight/dose.

9. The composition of claim 6, wherein the 28 kDa protein is present in a dosage amount of from about 38 to 3,800 mg/kg of body weight/dose.

* * * * *